(12) United States Patent
Lukenbach et al.

(10) Patent No.: US 7,074,747 B1
(45) Date of Patent: Jul. 11, 2006

(54) CLEANSING COMPOSITIONS

(75) Inventors: Elvin R. Lukenbach, Flemington, NJ (US); Claudia Kaminski, Milford, NJ (US); Sandrine Pascal-Suisse, Rouen (FR); Maurice Tahar, Vernon (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 331 days.

(21) Appl. No.: 09/604,449

(22) Filed: Jun. 27, 2000

Related U.S. Application Data
(60) Provisional application No. 60/141,927, filed on Jul. 1, 1999.

(51) Int. Cl.
*C11D 7/26* (2006.01)

(52) U.S. Cl. ...................................... 510/135; 510/505
(58) Field of Classification Search ................ 510/130, 510/135, 505
See application file for complete search history.

(56) References Cited

U.S. PATENT DOCUMENTS
4,337,166 A  6/1982  Hill et al. .............. 252/174.15

(Continued)

FOREIGN PATENT DOCUMENTS

| CA | 2 135 130 | 5/1995 |
|---|---|---|
| EP | 0 295 886 B1 | 12/1988 |
| EP | B-0370856 | 5/1990 |
| EP | 0 541 347 A2 | 5/1993 |
| GB | 2 250 998 | 6/1992 |
| JP | 7002677 | 1/1995 |
| WO | WO 95/05145 | * 2/1995 |
| WO | WO 95/05160 | 2/1995 |
| WO | WO 98/35652 | * 8/1998 |
| WO | WO 98/48768 | 11/1998 |
| WO | WO 98/51276 | 11/1998 |
| WO | WO 98/52528 | 11/1998 |
| WO | WO 98/54277 | 12/1998 |
| WO | WO 98/55576 | 12/1998 |

OTHER PUBLICATIONS

Search Report, WO 2001001949, Nov. 2000.*
English Translation of Taiwan Patent Application # 79/106,988, 1992.
English Translation of Taiwan Patent Application # 79/110,617, 1992.
English Translation of Japanese Patent JP 88/20407, 1988.
English Translation of EPO Patent EP 0 827 736 A1, 1998.
Gollnick, H. et al., "Sebaceous Glands, Acne and Related Disorder," *Dermatology*, 1998, 196(1), 119–125.
Piérard, G. E. et al., "New Insight into the Topical Management of Excessive Sebum Flow at the Skin Surface," *Dermatology*, 1998, 196(1), 126–129.
Toyoda, M. et al., "An Overview of Topical Antibiotics for Acne Treatment," *Dermatology*, 1998, 196(1), 130–134.
Meynadier, J. et al., "Systemic Antibiotics for Acne," *Dermatology*, 1998, 196(1), 135–139.

(Continued)

*Primary Examiner*—John R. Hardee

(57) ABSTRACT

Cleansing compositions suitable for use in personal cleansing applications, and in particular make-up removal applications, which not only impart superior cleansing properties, but also which are relatively non-irritating and thus suitable for use by people having sensitive skin and eyes comprised of esters, liquid silicones, and a water dispersible components. Also disclosed are compositions for effectively depositing various benefit agents into and onto the skin.

9 Claims, 9 Drawing Sheets

(7 of 9 Drawing Sheet(s) Filed in Color)

U.S. PATENT DOCUMENTS

| | | | |
|---|---|---|---|
| 4,741,855 A | 5/1988 | Grote et al. | 252/142 |
| 4,767,625 A | 8/1988 | Mitsuno et al. | 424/95 |
| 4,784,844 A | 11/1988 | Thimineur et al. | 424/65 |
| 4,980,155 A * | 12/1990 | Shah et al. | 424/63 |
| 4,992,477 A | 2/1991 | Geria | 514/782 |
| 5,043,155 A | 8/1991 | Puchalski et al. | 424/78 |
| 5,165,917 A | 11/1992 | Zabotto et al. | 424/70 |
| 5,217,641 A | 6/1993 | Herstein | 252/171 |
| 5,244,664 A | 9/1993 | Godtfredsen | 424/401 |
| 5,441,667 A | 8/1995 | Tonomura et al. | 252/174.15 |
| 5,451,254 A * | 9/1995 | Andrean et al. | 106/503 |
| 5,563,031 A | 10/1996 | Yu | 435/4 |
| 5,571,149 A | 11/1996 | Liss et al. | 607/72 |
| 5,599,800 A | 2/1997 | Candau et al. | 514/53 |
| 5,622,530 A | 4/1997 | Phipps | 604/20 |
| 5,624,676 A | 4/1997 | Mackey et al. | 424/414 |
| 5,661,189 A | 8/1997 | Grieveson et al. | 514/784 |
| 5,665,687 A | 9/1997 | Khayat et al. | 510/136 |
| 5,728,389 A | 3/1998 | Sebillotte-Arnaud | 424/400 |
| 5,735,273 A | 4/1998 | Kurnik et al. | 128/635 |
| 5,741,766 A | 4/1998 | Marion et al. | 510/130 |
| 5,749,847 A | 5/1998 | Zewert et al. | 604/49 |
| 5,756,437 A | 5/1998 | Yamazaki et al. | 510/136 |
| 5,766,575 A | 6/1998 | Crotty et al. | |
| 5,780,050 A | 7/1998 | Jain et al. | 424/449 |
| 5,789,255 A | 8/1998 | Yu | 536/95 |
| 5,791,766 A | 8/1998 | Lee | 362/259 |
| 5,804,540 A | 9/1998 | Tsaur et al. | 510/135 |
| 5,814,662 A | 9/1998 | Znaiden et al. | |
| 5,827,183 A | 10/1998 | Kurnik et al. | 600/345 |
| 5,843,114 A | 12/1998 | Jang | 606/186 |
| 5,865,788 A | 2/1999 | Edwards et al. | 604/22 |
| 5,869,326 A | 2/1999 | Hofmann | 435/285.2 |
| 5,871,756 A | 2/1999 | Jeffcoat et al. | |
| 5,888,951 A * | 3/1999 | Gagnebein et al. | 510/130 |
| 5,893,885 A | 4/1999 | Webster, Jr. | 607/122 |
| 5,897,553 A | 4/1999 | Mulier et al. | 606/41 |
| 5,906,613 A | 5/1999 | Mulier et al. | 606/41 |
| 5,989,572 A | 11/1999 | Habif et al. | |
| 5,993,434 A | 11/1999 | Dev et al. | 604/501 |
| 6,014,584 A | 1/2000 | Hofmann et al. | 604/21 |
| 6,055,043 A | 4/2000 | Chambers | 356/73.1 |
| 6,063,397 A | 5/2000 | Fowler et al. | 424/443 |
| 6,068,650 A | 5/2000 | Hofmann et al. | 607/2 |
| 6,096,020 A | 8/2000 | Hofmann | 604/501 |
| 6,117,660 A | 9/2000 | Walters et al. | 435/173.6 |
| 6,120,493 A | 9/2000 | Hofmann | 604/506 |
| 6,148,232 A | 11/2000 | Avrahami | 604/20 |
| 6,181,964 B1 | 1/2001 | Hofmann et al. | 604/21 |

OTHER PUBLICATIONS

Orfanos, C. E. et al., "Oral Retinoids in the Treatment of Seborrhoea and Acne," *Dermatology*, 1998, 196(1), 140–147.

Beylot, C. et al., "Oral Contraceptives and Cyproterone Acetate in Female Acne Treatment," *Dermatology*, 1998, 196(1), 148–152.

Schmidt, J. B., "Other Antiandrogens," *Dermatology*, 1998, 196(1), 153–157.

International Search Report PCT/US00/17431 dated Nov. 17, 2000, WO 01/001949.

* cited by examiner

Before Removal

2a Galenic
2b Cetaphil
2c pH 5.5 3-in-1
2d Vichy
2e F38626-015
2f Oil of Olay

Retinol Fluorescence 0.3% rol Cleanser

Retinol Fluorescence 0.3% rol Cleanser

Rinse off Luminosity Change =37.86

Wiped off Luminosity Change =27.19

Retinol Fluorescence 0.3% rol Cleanser

Retinol Fluorescence 0.3% rol Cleanser

Rinse off Luminosity Change =28.97

Wiped off Luminosity Change =17.01

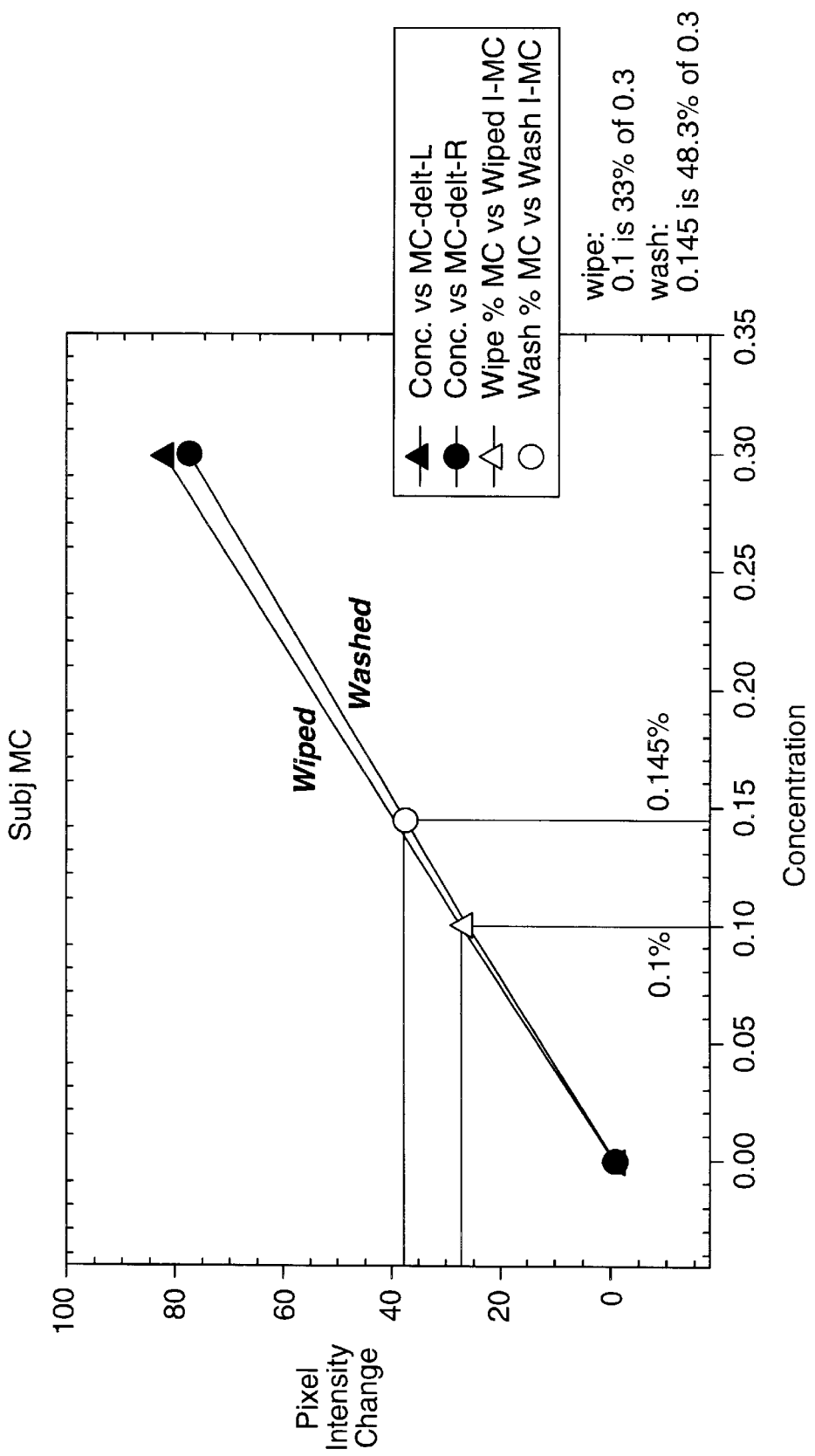

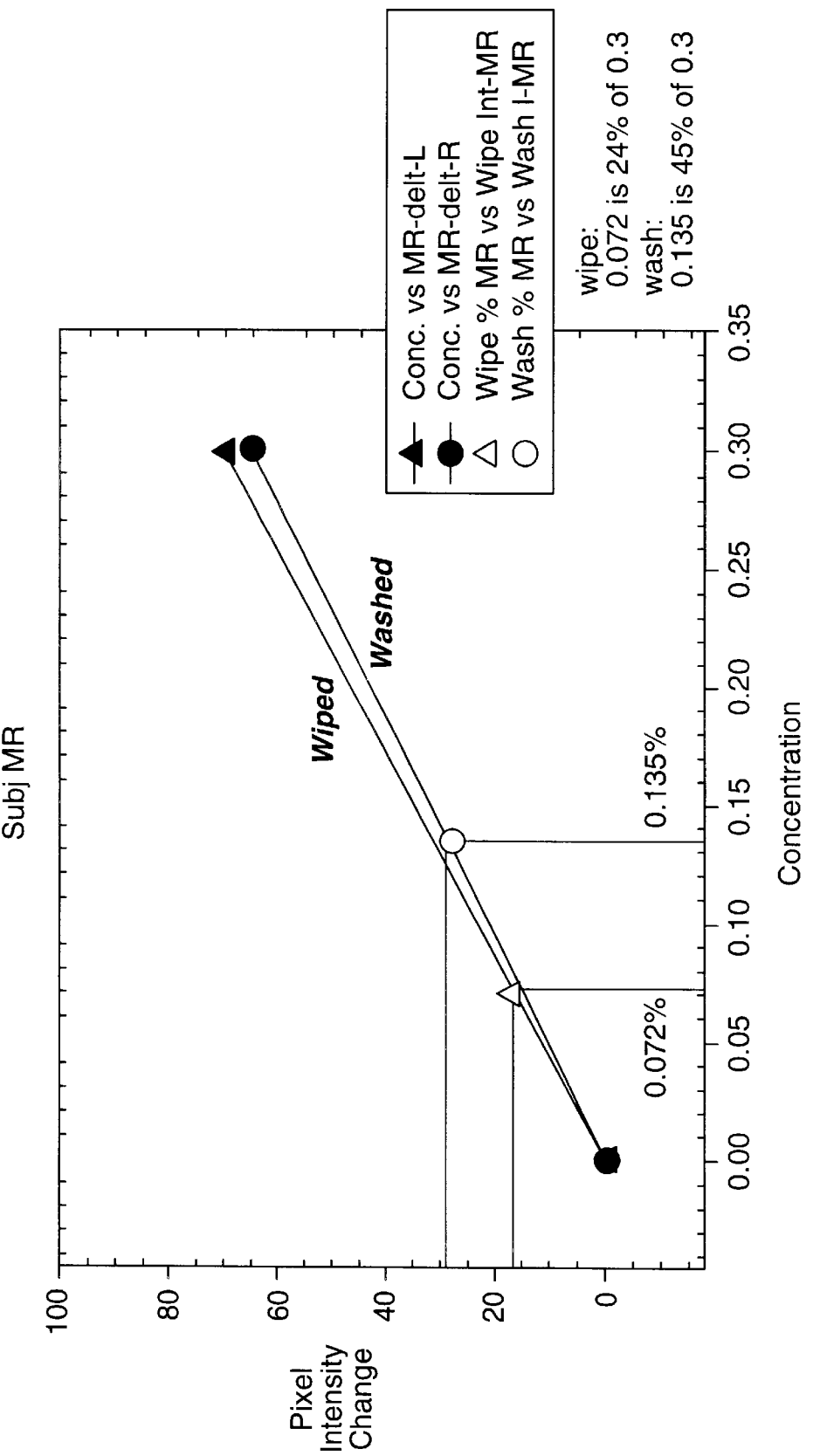

CLEANSING COMPOSITIONS

CROSS-REFERENCE TO RELATED APPLICATION

This application claims the benefit of U.S. Ser. No. 60/141927 filed 1 Jul. 1999 and PCT Application No. WO 2001001949 filed on 23 Jun. 2000, both of which are incorporated by reference herein in their entireties.

BACKGROUND OF THE INVENTION

1. Field of the Invention

This invention relates to cleansing compositions suitable for use in personal cleansing applications, and in particular make-up removal applications, which not only impart superior cleansing properties, but also which are relatively non-irritating and thus suitable for use by people having sensitive skin and dyes. This invention is further related to a composition for effectively delivering and/or depositing various benefit agents into and onto the skin.

2. Description of the Prior Art

Various types of cosmetics such as make-up, e.g. lipstick, mascara, foundation, and the like, leave an oil-containing residue on the skin surface that cannot be removed easily by facial cleansers containing conventional soaps. One reason is that such soaps are unable to effectively emulsify or solubilize such oils, which is why many make-up remover compositions have included an oil base as a major component. For example, European Patent No. 370856 discloses a non-foaming makeup remover system comprised of a surfactant-containing water phase that remains physically separated from a cosmetic oil-containing oil phase unless shaken. Disadvantageously, such oil-containing removers also suffer from a tendency to deposit an oily residue or film on the user's skin.

Various attempts have been made to produce stable, oil-free makeup removers. For example, U.S. Pat. No. 5,217,641 discloses an oil-free, stable, non-irritating, single-phase makeup remover comprised of 50 percent to 98 percent of cyclomethicone along with a mixture of esters. However, not only is it economically disadvantageous to use such a large amount of cyclomethicones, but because of their highly volatile nature, cyclomethicones cannot be packaged easily using conventional cosmetic packaging.

Another reason that make-up cannot be removed by conventional soaps is the fact that such soaps are incapable of removing the binders in the make-up. These binders tend to increase the make-up's resistance against sebum and water as well as its overall adhesiveness to the skin. In addition, various polymers, which are similarly difficult to remove, are also employed in hair cosmetics for the purpose of protecting the hair or providing the hair with body.

It would be desirable to have a stable, economically-feasible composition that could not only effectively remove the residue from sebum as well as the residue from make-up and hair-protecting agents, but also impart a pleasant, non-oily "after-feel" to the skin and hair. It would also be desirable to create such a composition having a low degree of ocular and skin irritation. It would further be desirable to create such a composition that is capable of depositing various active agents into and onto the skin.

SUMMARY OF THE INVENTION

In accordance with this invention, there is provided a cleaning composition comprising:
 a. a liquid silicone;
 b. a water dispersible component; and
 c. an ester.

Another embodiment of this invention is directed to a cleaning system comprising:
 a. a liquid silicone;
 b. a water dispersible component;
 c. an ester;
 d. water; and
 e. a polymeric emulsifier and/or thickener.

Another embodiment of this invention is directed to a foaming composition comprising:
 a. a water dispersible component;
 b. an ester;
 c. water, and a
 d. foaming surfactant.

Yet another embodiment of the present invention is directed to a method for making an oil-in water emulsion comprised of:
 neutralizing a hydrophilic thickening agent in a hydrophilic phase comprised of a polymeric emulsifier with an effective amount of a neutralizer under conditions sufficient after a lipophilic phase was combined with the hydrophilic phase.

Yet another embodiment of the present invention is directed to a method for making a water-in-oil emulsion comprised of:
 neutralizing a hydrophilic thickening agent in a hydrophilic phase comprised of a polymeric emulsifier with an effective amount of a neutralizer under conditions sufficient before combning a lipophilic phase with the hydrophilic phase.

Yet another embodiment of the present invention is directed to a method for depositing benefit agents into and onto the skin comprised of:
 topically applying an effective amount of the benefit agent with a composition comprised of an optional liquid silicone, a water dispersible component, and an ester to a desired location.

Yet another embodiment of the present invention is directed to a method for depositing a benefit agent into and/or onto the skin, hair and/or nails comprising applying a composition comprising:
 a. an optional liquid silicone;
 b. a water dispersible component;
 c. an ester;
 d. a polymeric emulsifier and/or thickener; and
 e. an effective amount of a benefit agent to a desired location on a human or animal.

Yet another embodiment of the present invention is directed to a method for depositing a benefit agent into and/or onto the skin, hair and/or nails comprising applying a composition comprising:
 a. an optional liquid silicone;
 b. a water dispersible component
 c. an ester;
 d. water;
 e. a foaming surfactant; and
 f. an effective amount of a benefit agent to a desired location on a human or animal.

The compositions of this invention are capable of effectively cleansing the skin without significantly contributing to ocular irritation as well as depositing various benefit agents into and into the skin, hair and nails.

DESCRIPTION OF THE DRAWINGS

The file of this patent contains at least one drawing executed in color. Copies of this patent with color drawing(s) will be provided by the Patent and Trademark Office upon request and payment of the necessary fee.

The invention will be more fully understood and further advantages will become apparent when reference is made to the following detailed description of the invention and the accompanying drawing in which:

FIG. 5(a) Is a graph of concentration of retinol in the formulation of Example 10 versus pixel intensity change.

FIG. 5(b) is a graph of concentration of retinol in the formulation of Example 11 versus pixel intensity change.

DETAILED DESCRIPTION OF PREFERRED EMBODIMENTS

Figure 1:
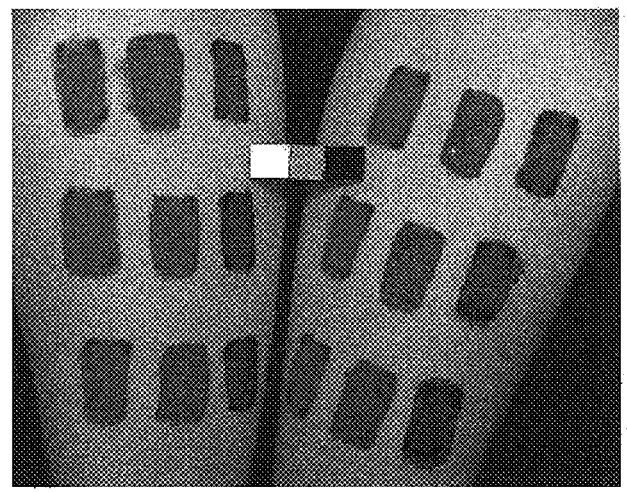
FIG. 1 is a representation that illustrates two forearms, each of which contains three sets of three different types of makeup before a cleanser is applied thereto.
Figure 2:
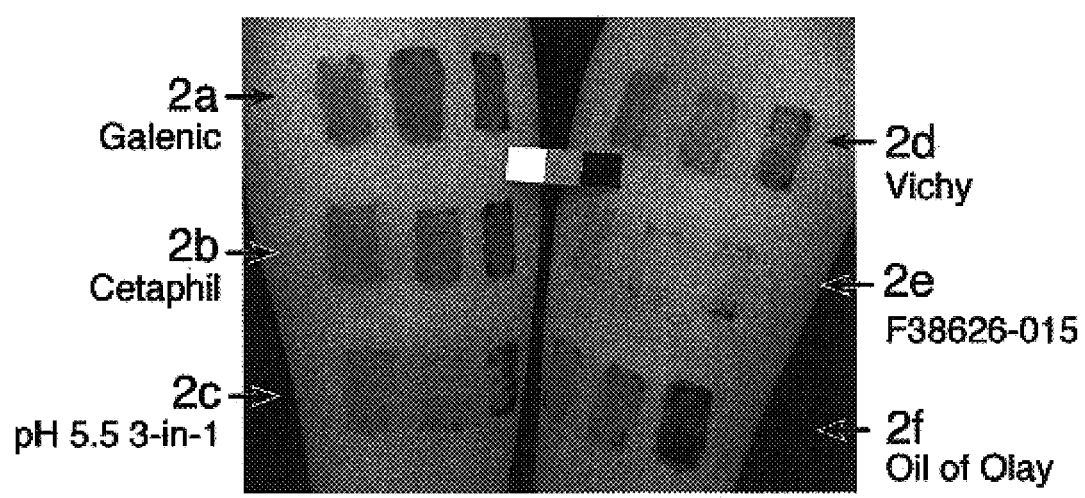
FIGS. 2 (a) through (f) are representations of the same forearm after six respective cleansers were applied to each set of makeup, respectively.

In one embodiment of the present invention, the cleaning composition may suitably comprise, consist of, or consist essentially of, based upon the total weight of the cleaning composition, a) from about 10 percent to about 35 percent, and preferably from about 10 percent to about 20 percent of a liquid silicone; b) from about 10 percent to about 35 percent, and preferably from about 10 percent to about 20 percent of a water dispersible component; and c) from about 30 percent to about 80 percent, and preferably from 55 percent to about 65 percent of an ester.

The first component of the cleaning composition of the present invention may be either a volatile or nonvolatile liquid silicone, with the former being preferred. Examples of suitable silicones nonexclusively include the polydimethyl siloxanes and derivatives thereof such as hexamethylsiloxane, dimethicone, dimethiconol, and cyclomethicone, with cyclomethicone being preferred. Examples of suitable cyclomethicones nonexclusively include cyclotetradimethyl siloxane; cyclopentadimethyl siloxane, cyclohexadimethyl siloxane, cycloheptadimethyl siloxane, and mixtures thereof. Preferably, the silicone has a viscosity of from about 0.25 cp to about 350 cp.

The second component of the cleaning composition of the present invention is a water dispersible component, which is preferably a water soluble solvent. As used herein, the term "water dispersible component" shall mean a material that produces a uniform, clear or hazy, mixture when combined with at least a weight equivalent of water. Examples of suitable water dispersible components nonexclusively include polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof. Most preferred water dispersible components include hexylene glycol, dimethyl isosorbide, polyethylene glycol-6 caprylic/capric glyceride, and mixtures thereof.

The third component of the cleaning composition of the present invention is a lipophilic component that preferably is a liquid ester. Preferred esters for use in the composition of this invention include those liquid esters that either possess a structural means for ensuring its liquidity or are heterogeneous in nature. Examples of such structural means include the presence of "interruptions", such as: 1) chain branching; 2) olefinic unsaturation; 3) the presence of either a polyether or a monoalkoxylate in the structure; or 4) the presence of a substituent, e.g. an ethoxylated or propoxylated moiety, bonded between the acid group and the alcohol group. By "heterogeneity," it is meant that the lipophilic component is comprised of a mixture of compounds that vary in the number of carbon atoms in their respective chains.

Examples of suitable esters nonexclusively include:

a) a branched $C_5$ to $C_{22}$ alkyl alcohol ester of an aromatic acid;

b) a straight-chained or branched $C_5$ to $C_{22}$ alkyl acid esters of optionally ethyoxylated/propoxylated polyols having from about 3 carbon atoms to about 7 carbon atoms;

c) branched $C_5$ to $C_{22}$ alkyl alcohol esters of branched polyacids;

d) branched or straight-chained $C_5$ to $C_{22}$ alkyl acid esters of branched and/or unsaturated $C_5$ to C22 alkyl alcohols;

e) branched or unsaturated $C_5$ to $C_{22}$ alkyl alcohol esters of an acid selected from the group consisting of adipic acid, succinic acid, maleic acid, sebacic acid, and mixtures thereof f) polyether interrupted fatty acid esters;

g) benzoic acid ester of heterogeneous alcohols having from about 8 carbon atoms to about 22 carbon atoms; and h) mixtures thereof, with straight-chained or branched $C_5$ to $C_{22}$ alkyl acid esters of optionally ethyoxylated/propoxylated polyols, benzoic acid esters of heterogeneous alcohols, and mixtures thereof being particularly preferred.

Suitable branched $C_5$ to $C_{22}$ alkyl alcohol esters of an aromatic acid include those wherein the aromatic acid is benzoic acid. Preferably, the alcohol of this ester is either branched or unsaturated, and may be either a primary alcohol or a secondary alcohol with the former being preferred. Optionally, the aromatic acid may be substituted with hydroxy or alkyl groups having from about 1 carbon atom to about 4 carbon atoms. Specific examples of these esters nonexclusively include, butyloctyl salicylate; hexyldecyl benzoate; and butyloctyl benzoate, which are all available from C.P. Hall Co. under the tradename, "HallStar;" and mixtures thereof, with a mixture of hexyldecyl benzoate and butyloctyl benzoate being particularly preferred.

Another suitable ester includes a straight-chained or branched $C_5$ to $C_{22}$ alkyl acid ester of optionally ethyoxylated/propoxylated polyols, wherein the polyols contain from about 3 carbon atoms to about 7 carbon atoms. Preferably, if the polyol creates a branching point, then the acid group may be straight-chained. Suitable acids used to form these esters typically have from about 8 carbon atoms to about 22 carbon atoms, and preferably from about 8 carbon atoms to about 18 carbon atoms, and most preferably from about 8 carbon atoms to about 12 carbon atoms, and are either saturated or unsaturated, with octanoic acid, capric acid, and mixtures thereof being preferred. Such suitable acids are either straight-chained or branched, and are preferably aliphatic. Suitable polyols used to form these esters typically have from about 3 carbon atoms to about 30 carbon atoms, and preferably from about 3 carbon atoms to about 7 carbon atoms. Examples of such suitable polyols nonexclusively include neopentyl alcohol; polyglycerol, e.g. diglycerol, triglycerol, hexaglycerol, and decaglycerol, wherein the polyglycerol may contain from about 2 to about 10 glycerol groups; glycerin; sorbitan; methyl glucose; trimethylolpropane; and mixtures thereof. Neopentyl alcohol, glycerin, trimethylolpropane, and mixtures thereof are the preferred polyols. Examples of suitable esters nonexclusively include pentaerythritol tetraoctanoate; trimethylolpropane trioctanoate; trioctanoin; pentaerythrityl tetrapelargonate; sorbitan trioleate; caprylic/capric triglyceride; neopentyl alcohol tetraoctanoate, and mixtures thereof, with caprylic/capric triglyceride; pentaerythritol tetraoctanoate; trimethylolpropane trioctanoate; and pentaerythrityl tetrapelargonate being more preferred.

Another suitable ester includes the branched $C_5$ to $C_{22}$ alkyl alcohol esters of branched polyacids such as the tri-esters, tetra-esters, penta-esters, and mixtures thereof. An example of such a polyacid is citric acid. Suitable alkyl alcohols for creating these esters are optionally substituted, e.g., ethoxylated or propoxylated, contain from about 3 carbon atoms to about 22 carbon atoms, and preferably from about 3 carbon atoms to about 8 carbon atoms, and are either straight-chained or branched, with the branching being preferred. These alcohols may either be primary or secondary, and may either be saturated or unsaturated, with saturated being preferred for stability reasons. Specific examples of suitable esters nonexclusively include trioctyldodecyl citrate; triisopropylcitrate; and mixtures thereof.

Another suitable ester includes the branched or straight-chained $C_6$ to $C_{22}$ alkyl acid esters of branched or unsaturated alkyl alcohols wherein the alkyl group of the alcohol has from about 1 carbon atoms to about 18 carbon atoms, and preferably from about 4 carbon atoms to about 10 carbon atoms, provided that the total number of carbon atoms in the ester is at least about 8. Suitable acids for use in making these esters typically have from about 2 carbon atoms to about 22 carbon atoms, and preferably from about 5 carbon atoms to about 10 carbon atoms. However, if the number of acid carbon atoms exceeds the number of carbon atoms in the alcohol, then the acid preferably contains from about 8 carbon atoms to about 18 carbon atoms and the alcohol preferably contains from about 1 carbon atom to about 8 carbon atoms. If the number of acid carbon atoms is less than the number of carbon atoms in the alcohol, then the acid preferably contains from about 2 carbon atoms to about 8 carbon atoms and the alcohol preferably contains from about 8 carbon atoms to about 18 carbon atoms. Preferably, either: 1) the alcohol group or the acid group has branching and/or unsaturation, i.e. both the alcohol and the acid are not straight-chained; or 2) the ester possesses an asymmetrical alkyl distribution. By "asymmetrical alkyl distribution," it is meant that the ester is made from, for example, a short chain alcohol, i.e. having from about 1 carbon atom to about 8 carbon atoms, and a long chain acid, i.e., having greater than about 8 carbon atoms, such as, e.g. butyl stearate, or less preferably the ester is made from, a long chain alcohol, i.e. having greater than about 8 carbon atoms, and a short chain acid, i.e. having from about 1 carbon atom to about 8 carbon atoms. Examples of such suitable esters nonexclusively include tridecyl neopentanoate, isostearyl palmitate, cetyl ricinoleate, cetyl octanoate, isononyl isononanoate, butyl stearate, octyldodecyl soyate, tridecyl erucate, octyldodecyl erucate/eicosil erucate, and mixtures thereof, with cetyl octanoate, isostearyl palmitate, isononyl isononanoate, and mixtures thereof and being preferred.

Another suitable ester includes the branched or unsaturated $C_5$ to $C_{22}$ alkyl alcohol esters of an acid selected from the group consisting of adipic acid, succinic acid, maleic acid, sebacic acid, and mixtures thereof. The alcohol of these esters, which has from about 3 carbon atoms to about 18 carbon atoms, and preferably from about 3 carbon atoms to about 8 carbon atoms, Is preferably branched or unsaturated. Examples of such suitable alcohol esters nonexclusively include diisopropyl adipate, dioctyl sebacate, dioctyl succinate, dioctyl maleate, diisostearyl adipate, diethyl sebacate, and mixtures thereof, with diethyl sebacate, dioctyl sebacate, and diisostearyl adipate being preferred.

Another suitable ester includes polyether interrupted fatty acid esters. Examples of such suitable esters nonexclusively include: 1) laureth-2 benzoate; 2) $C_8$ to $C_{22}$ fatty alkyl (optionally polypropylenoxy) polyethyleneoxy carboxylate esters derived from an alcohol having from about 1 carbon atom to about 22 carbon atoms, is either straight or branched, and may contain a phenyl group; and 3) mixtures thereof, with $C_8$ to $C_{22}$ fatty alkyl (optionally polypropylenoxy) polyethyleneoxy carboxylate esters being preferred. Specific examples of preferred esters nonexclusively include isopropyl propylene glycol-2-isodeceth-7 carboxylate, such as "Velsan D8P3" and other commercially available materials sold by Sandoz under the tradename, "Velsan."

Another suitable ester includes the benzoic acid esters of heterogeneous alcohols having from about 8 carbon atoms to about 22 carbon atoms, such as the ester mixtures available from Finetex under the tradename, "Finsolv" and preferably is the $C_{12}$ to $C_{15}$ alcohols benzoate available from Finetex under the tradename, "Finsolv TN."

Preferred combinations of esters include at least one, preferably at least two, and more preferably three of the following esters: a) branched $C_5$ to $C_{22}$ alkyl alcohol esters of an aromatic acid; b) branched or straight-chained $C_5$ to $C_{22}$ alkyl acid esters of branched or unsaturated alkyl alcohols; and c) straight-chained or branched $C_5$ to $C_{22}$ alkyl acid esters of optionally ethyoxylated/propoxylated polyols. In a preferred embodiment, the ester contains, based upon the total weight percent of the esters, from about 30 percent to about 80 percent of branched or straight-chained $C_5$ to $C_{22}$ alkyl acid esters of branched or unsaturated $C_5$ to $C_{22}$ alkyl alcohols; from about 10 percent to about 50 percent of branched $C_5$ to $C_{22}$ alkyl alcohol esters of an aromatic acid; and from about 10 percent to about 50 percent of straight-chained or branched $C_5$ to $C_{22}$ alkyl acid esters of optionally ethyoxylated/propoxylated polyols. In a more preferred embodiment, the ester contains, based upon the total weight percent of the esters, from about 15 percent to about 50 percent isononyl isononanoate, from about 15 percent to about 50 percent isostearyl palmitate, from about 15 percent to about 50 percent cetyl octanoate, and from about 15 percent to about 50 percent pentaerthritol tetraoctanoate.

Another embodiment of the present invention is directed to a cleaning system comprising, consisting, or consisting essentially of, based upon the total weight of the cleaning system, a) at least 5 percent and preferably at least about 10 percent of the cleaning composition; b) from about 70 percent to about 98 percent, and preferably from about 80 percent to about 90 percent of water; c) from about 0.1 percent to 5 percent, e.g. from about 0.5 percent to about 1.5 percent of a polymeric emulsifier, a thickener, or mixture thereof, optionally d) from about 0.1 percent to about 9 percent, and preferably from about 1 percent to about 3 percent of a cleaning enhancer; optionally a) from about 2 percent to about 20 percent, and preferably from about 5 percent to about 15 percent of a foaming surfactant; and optionally f) from about 0.001 percent to about 5 percent of a benefit agent. In one embodiment, the cleaning system may comprise, based upon the total weight of the cleansing system, from about 0.1 to about 5 percent, and preferably from about 0.5 percent to 1.5 percent of a polymeric emulsifier and/or from about 0.01 percent to about 2 percent, and preferably from about 0.01 percent to about 0.5 percent of a thickener. More preferably, the cleaning system contains, based upon the total weight of the cleaning system, from about 10 percent to about 30 percent of the cleaning composition.

The cleaning system may be in the form of an oil-in-water emulsion, a water-in-oil emulsion, or a dispersion.

In addition to the cleansing composition, the cleaning system is further comprised of polymeric emulsifiers and/or thickeners. As used herein, the term "polymeric emulsifiers" shall mean those compounds capable of emulsifying cleaning systems whereby the polymeric emulsifiers have a molecular weight of at least about 5000, and preferably are block copolymers having a hydrophilic portion and a hydrophobic portion. When used at amounts effective for emulsifying the cleansing system, the polymeric emulsifiers surprisingly do not cause significant eye sting, i.e., when the emulsifer-containing composition was used by 80 consumers in the eye area, no more than about 5% of such users expressed discomfort around the eye area. Examples of suitable polymeric emulsifiers nonexclusively include polyethylene glycol-30 dipolyhydroxystearate available from Uniqema under the tradename, 'Arlacel P-135;" dimethicone copolyol, which is available from Goldschmidt Chemical Corporation under the tradename, "Abil EM 90"; substituted acrylates such as those available from The Goodrich Corporation under the tradename, "Pemulen"; and mixtures thereof, with polyethylene glycol-30 dipolyhydroxystearate being preferred.

Examples of suitable hydrophilic thickeners nonexclusively include carbomers available from B.F. Goodrich under the tradename, "Carbopol ETD 2020", acrylate copolymers, hydroxyethylcellulose modified with cetyl ether groups available from Hercules under the tradename, "Natrosol Plus", polyvinylmethyl ether/maleic anhydride (PVM/MA) decadiene crosspolymer available from International Specialty Products under the tradename, "Stabileze QM," and copolymers and mixtures thereof, with carbomers being preferred. Examples of suitable acrylate copolymers nonexclusively include acrylate copolymers available from Rohm & Haas under the tradename, "Aculyn 33," acrylates/aminoacrylates copolymer available from National Starch & Chemical Company under the tradename, "Structure Plus," acrylates/steareth-20 itaconate copolymer available from National Starch & Chemical Company under the tradename, "Structure 2001," acrylates/ceteth-20 itaconate copolymer available from National Starch & Chemical Company under the tradename, "Structure 3001," acrylates/steareth-20 methacrylate copolymer available from Rohm & Haas under the tradename, "Aculyn 22," and copolymers and mixtures thereof.

The cleaning system of the present invention may also optionally contain a cleaning enhancer in the form of a nonionic emulsifier and/or a non-foaming surfactant. Examples of suitable nonionic emulsifiers include isocetheth-20, oleth-2, mixture of PEG-40 hydrogenated castor oil and trideceth-9 available from Dragoco Inc. under the tradename, "Dragoco Solubilizer 2/014160," Poloxamer 184, laureth-4, sorbitan trioleate, polyoxyethylene-(2) oleyl ether, sorbitan stearate, cetearyl glucoside, glyceryl oleate, trideceth-9, polyethylene glycol-40 hydrogenated castor oil, and mixtures thereof.

Examples of suitable non-foaming surfactants include non-foaming nonionic surfactants such as sucrose esters, e.g., sucrose cocoate, sucrose stearate and mixtures thereof, with sucrose cocoate being preferred. By "essentially non-foaming," it is meant that the surfactant, when used with the composition of the present invention, has a column height of less than about 20 mm as determined by the Ross-Miles Foam Generation Test. See 18 (I.) Oil & Soap 99–102 (1941)("Ross-Miles Test"), which is incorporated by reference herein. The cleansing composition and the cleansing system may either be rinseable with water or may be wiped-off. Preferably, the essentially, non-foaming surfactants are used in embodiments wherein the cleansing system or the cleansing composition is rinseable with water. For example, a preferred combination of hydrophilic components include, based upon the total weight percent of the cleansing system, from about 0.1 percent to about 5.0 percent of hexylene glycol, from about 0.5 percent to about 3.0 percent of sucrose cocoate non foaming surfactant, and from about 0.5 percent to about 3.0 percent of polyoxyethylene-6 caprylic/capric triglyceride. An example of a suitable cleaning enhancer include a mixture of sorbitan stearate and sucrose cocoate available from Uniqema under the tradename, "Arlatone 2121."

Preferably, the cleaning system contains, based upon the total weight of the cleansing system, no more than about 6%, and preferably 5%, of the cleaning enhancers for cream formulations and no more than about 2%, and preferably no more than 1% of the cleaning enhancers in thin lotion/milk formulations.

The cleansing system and cleansing composition may also optionally contain a foaming surfactant. The foaming surfactant may be non-ionic, cationic, amphoteric, or anionic; nonionic surfactants are preferred. By "foaming," it is meant that the surfactant, when used with the composition of the present invention, has a column height of foam greater than about 20 mm as determined by the Ross-Miles Test. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. Examples of suitable and preferred surfactants may be found in International Patent Application Number WO97/01196, which is incorporated by reference in its entirety herein.

The cleansing system may further contain one or more benefit agents or pharmaceutically-acceptable salts thereof. As used herein, the term "benefit agent" includes any active ingredient that is to be delivered into and/or onto the skin, hair or nail at a desired location, such as a cosmetic agent or a pharmaceutical agent. By "cosmetic agent," it is meant any ingredient that is appropriate for cosmetically treating, providing nutrients to, and/or conditioning the hair, nail, and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

The benefit agents useful herein may be categorized by their therapeutic benefit or their postulated mode of action. However, it is to be understood that the benefit agents useful herein may, in some circumstances, provide more than one thereapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the cleansing composition/cleansing system.

Examples of suitable benefit agents include, but are not limited to, depigmentation agents; reflectants; detangling/wet combing agents; film forming polymers; humectants; amino acids and their derivatives; antimicrobial agents; allergy inhibitors; anti-acne agents; anti-aging agents; anti-wrinkling agents antiseptics; analgesics; antifussives; antipruritics; local anesthetics; anti-hair loss agents; hair growth promoting agents; hair growth inhibitor agents, antihistamines such as *Mandragora Vernalis, Tanacetum Parthenium* and the like; antiinfectives such as *Acacia Catechu, Aloe Barbadensis, Convallaria Majalis, Echinacea, Eucalyptus, Mentha Piperita, Rosa Canina, Sassafras Albidum*, and the like; inflammation inhibitors; anti-emetics; anticholinergics; vasoconstrictors; vasodilators; wound healing promoters; peptides, polypeptides and proteins; deodorants and antiperspirants; medicament agents; skin emollients and skin moisturizers; skin firming agents, hair conditioners; hair softeners; hair moisturizers; vitamins; tanning agents; skin lightening agents; antifungals such as *Centaurea Cyanus*, Kalmia Latifolia and antifungals for foot preparations; depilating agents; shaving preparations, external analgesics; perfumes; counterirritants; hemorrhoidals; insecticides, poison ivy products; poison oak products; burn products; antidiaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens, those active ingredients disclosed in U.S. Pat. No. 6,063,397, which is incorporated herein by reference, anti-edema agents, collagen enhancers, and mixtures thereof.

Examples of suitable anti-edema agents nonexclusively include bisabolol natural, synthetic bisabolol, and mixtures thereof.

Examples of suitable vasoconstrictors nonexclusively include horse chestnut extract, prickly ash, and mixtures thereof.

Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene including "Lyc-o-Pen" available from LycoRed Natural Products Industries, Ltd., oat oil, chamomile, and mixtures thereof.

Examples of collagen enhancers nonexclusively include vitamin A, vitamin C, and mixtures thereof.

Examples of suitable skin firming agent nonexclusively include dimethylaminoethanol ("DMAE").

Examples of suitable antipruritics and skin protectants nonexclusively include oatmeal, betaglucan, feverfew, soy and derivatives thereof, bicarbonate of soda, colloidal oatmeal, surfactant based colloidal oatmeal cleanser, Anagallis Arvensis, Oenothera Biennis, Verbena Officinalis, and the like. These antipruritics may be used in an amount, based upon the total weight of the cleansing composition, from about 0.01 percent to about 40 percent, and preferably from about 1 percent to about 5 percent.

As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation and colloidal oatmeals available from Quaker.

Examples of suitable reflectants nonexclusively include mica, alumina, calcium silicate, glycol dioleate, glycol distearate, silica, sodium magnesium fluorosilicate, and mixtures thereof.

Suitable detangling/wet combing agents nonexclusively include polyquaternium-10, hydroxypropyltrimonium guar, dioleoylamidoethyl hydroxyethylmonium methosulfate, di-(soyoylethyl) hydroxyethylmonium methosulfate, hydroxyethyl behenamidopropyl dimonium chloride, olealkonium chloride, polyquaternium-47, stearalkonium chloride, tricetylmonium chloride, and mixtures thereof.

Suitable film forming polymers include those that, upon drying, produce a substantially continuous coating or film on the heir, skin, or nails. Nonexclusive examples of suitable film forming polymers include acrylamidopropyl trimonium chloride/acrylamide copolymer; corn starch/acrylamide/sodium acrylate copolymer, polyquaternium-10; polyquaternium-47; polyvinylmethylether/maleic anhydride copolymer; styrene/acrylates copolymers; and mixtures thereof.

Commercially available humectants which are capable of providing moisturization and conditioning properties to the cleansing composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula I.:

$$HO-(R''O)_b-H \qquad \text{I.}$$

wherein R" is an alkylene group having from about 2 to about 4 carbon atoms and b is an integer of from about 1 to about 10, such as PEG 4; 3) polyethylene glycol ether of methyl glucose of formula II.:

$$CH_3-C_6H_{10}O_5-(OCH_2CH_2)_c-OH \qquad II.$$

wherein c is an integer from about 5 to about 25; 4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, capryloyl collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A,C, D,E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

Examples of suitable hair conditioners nonexclusively include quaternized compounds such as behenamidopropyl PG-dimonium chloride, tricetylmonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable Insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula III.

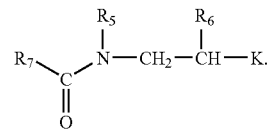

III wherein
R$_5$ is a branched or unbranched alkyl group having about 1 to about 6 carbon atoms;
R$_6$ is H, methyl or ethyl;
R$_7$ is a branched or unbranched alkyl or alkoxy group having from about 1 to about 8 carbon atoms; and
K is a —CN or a —COOR$_6$ group, wherein
R$_6$ is a branched or unbranched alkyl group having from about 1 to about 6 carbon atoms,
natural or synthetic pyrethroids, whereby the natural pyrethroids are contained in pyrethrum, the extract of the ground flowers of *Chrysanthemum cinerariaefolium* or *C. coccineum*; and mixtures thereof. Within the structure of Formula III are ethyl 3-(N-butylacetamido)propionate, wherein R$_7$ is a CH$_3$ group, R$_5$ is an n-butyl group, R$_6$ is H, K is COOR$_8$ and R$_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, *Fragaria Vesca*, *Matricaria Chamomilla*, and *Salvia Officinalis*.

Examples of suitable hemorrhoidal products nonexclusively include the anesthetics such as benzocaine, pramoxine hydrochloride, and mixtures thereof; antseptics such as benzethonium chloride; astringents such as zinc oxide, bismuth subgallate, balsam Peru, and mixtures thereof; skin protectants such as cod liver oil, vegetable oil, and mixtures thereof.

Most preferred benefit agents nonexclusively include DMAE, soy and derivatives thereof, colloidal oatmeal, sulfonated shale oil, olive leaf, elubiol, 6-(1-piperidinyl)2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatves thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the cleansing composition or the emulsion may vary depending upon, for example, the ability of the benefit agent to penetrate through the skin, hair or nail, the specific benefit agent chosen, the particular benefit desired, the sensitivity of the user to the benefit agent, the health condition, age, and skin, hair, and/or nail condition of the user, and the like. In sum, the benefit agent is used in a "safe and effective amount," which is an amount that is high enough to deliver a desired skin, hair or nail benefit or to modify a certain condition to be treated, but is low enough to avoid serious side effects, at a reasonable risk to benefit ratio within the scope of sound medical judgment. Unless otherwise expressed herein, typically the benefit agent is present in the cleansing system in an amount, based upon the total weight of the system, from about 0.01 percent to about 20.0 percent, and preferably from about 0.01 percent to about 5.0 percent, and more preferably from about 0.01 percent to about 2.0 percent.

Optionally, commercially available detergent thickeners that are capable of imparting the appropriate viscosity to conditioning shampoo compositions are suitable for use in this invention. If used, the detergent thickeners should be present in the shampoo compositions in an amount sufficient to raise the Brookfield viscosity of the composition to a value of between about 500 to about 10,000 centipoise. Examples of suitable detergent thickeners nonexclusively include: mono or diesters of polyethylene glycol of formula IV.

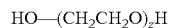

$$HO-(CH_2CH_2O)_zH \qquad \qquad IV.$$

wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable detergent thickeners nonexclusively include behenalkonium chloride; cetyl alcohol, quaternium-46, hydroxyethyl cellulose, cocodimonium chloride, polyquaternium-6, polyquaternium-7, quaternium-18, PEG-18 glycerol oleate/cocoate, a mixture of acrylates/steareth-50 acrylate copolymer, laureth-3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred detergent thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

The above described cleansing composition and cleaning system may be prepared by combining the desired components in a suitable container and mixing them under ambient conditions in any conventional mixing means well known in the art, such as a mechanically stirred propeller, paddle, and the like.

In another preferred embodiment of the cleaning system of the present invention wherein a polymeric emulsifier such as, for example, polyethylene glycol-30 dipolyhydroxystearate (hereinafter "PEG 30") or dimethicone copolyol, are used and water is used as the vehicle, an oil-in-water emulsion may be produced. Although both the PEG 30 and dimethicone copolyol are marketed for use in formulating water-in-oil compositions, we have unexpectedly found that oil-in-water emulsions may be created due to the unique processing steps and conditions employed herein. More specifically, we found that when a thickening agent, preferably a hydrophilic thickening agent, is neutralized in the hydrophilic phase of the present invention comprising a polymeric emulsifier prior to adding the lipophilic phase of the present invention thereto, the resulting emulsion is in the form of a water-in-oil emulsion. Conversely, when a thickening agent, preferably a hydrophilic thickening agent, is neutralized in the hydrophilic phase of the present invention comprising a polymeric emulsifier after the lipophilic phase of the present invention is added to the hydrophilic phase, the resulting emulsion is unexpectedly in the form of a oil-in-water emulsion.

Cleansing systems of the present invention that are emulsions may contain, based upon the total weight of the emulsion, from about 0.01 percent to about 2 percent, and preferably from about 0.01 percent to about 0.5 percent of hydrophilic thickeners. Suitable neutralizers include any known bases, such as sodium hydroxide, or acids, such as lactic acid, that are capable of neutralizing the hydrophilic thickening agent, in either the hydrophilic phase (if a water-in-oil emulsion is desired) or a mixture of both the hydrophilic phase and the lipophilic phase (if an oil-in-water emulsion is desired) of the present invention to a pH of about 5 to about 7 under ambient temperature. In one embodiment, hydrophilic thickeners including acrylates/aminoacrylates copolymer, acrylates/steareth-20 itaconate copolymer, acrylates/ceteth-20 itaconate copolymer, are preferably neutralized with an acid, such as lactic acid. Hydrophilic thickeners including carbomers, modified hydroxyethylcellulose, polyvinylacetate/maleic anhydride (PVA/MA) decadiene crosspolymer, and acrylates/steareth-20 methacrylate copolymer, are preferably neutralized with a base, such as sodium hydroxide (20%).

In one embodiment, the hydrophilic phase may be comprised of one or more of the following components: water, thickener, cleansing enhancer, nonfoaming surfactant, and water dispersible component, and the lipophilic phase may be comprised of one or more of the following components: silicone, ester, and polymeric emulsifier.

We have also surprisingly found that the cleansing system of the present invention possesses good aesthetic properties without causing any significant ocular discomfort to the user. It is well-known in the art that most emulsifiers having a relatively low molecular weight are irritating regardless of their hydrophilic lipophilic balance ("HLB") value. However, we have surprisingly found that when the cleansing system of the present invention is produced using the particular polymeric emulsifiers and/or thickeners set forth herein, the resulting cleanser is gentle and possesses a low degree of ocular and skin irritation.

Another embodiment of this invention is directed to a foaming composition comprising, based upon the foaming composition, from about 0.1 percent to about 30 percent, e.g. from about 0.1 percent to about 5 percent of a water dispersible component; from about 0.1 percent to about 30 percent, e.g. from about 0.1 percent to about 5 percent of an ester; from about 1.0 percent to about 98 percent, e.g. from about 30 percent to about 98 percent or from about 45 percent to about 90 percent of water; and from about 2.0 percent to about 20 percent, e.g. from about 5.0 percent to about 15 percent of a foaming surfactant. Optionally, the foaming composition may also be comprised of one or more of the following components, based upon the total weight of the foaming composition: a) from about 0.1 percent to 5 percent, e.g. from about 0.5 percent to about 1.5 percent of a polymeric emulsifier, a thickener, or mixture thereof; b) from about 0.1 percent to about 5 percent, e.g. from about 1 percent to about 3 percent of a cleaning enhancer; c) from about 0.001 percent to about 5 percent of a benefit agent; and d) from about 0.1 percent to about 30 percent, e.g. from about 0.1 percent to about 5 percent of a liquid silicone.

Another embodiment of the present invention is directed to a method for depositing a benefit agent onto the skin, hair and/or nails comprised of applying either the above-described cleansing system or cleansing composition with an effective amount of a benefit agent to a desired location on a human or animal. While the frequency and amount of the benefit agent-containing cleaning system to be applied will depend upon, for example, the type and amount of benefit agent available, the intended usage of the final composition, i.e. therapeutic versus maintenance regimen, the amount and type of detergent present, and the sensitivity of the individual user to the composition/emulsion, typically the benefit agent-containing cleaning system of the present invention should be topically applied to affected body parts at regular intervals, and preferably from about 2 to about 14 times per week. More preferably, the composition/emulsion is applied more frequently during the initial stages of treatment, e.g. from about 5 to about 7 times per week until the desired effect is achieved, then less frequently when maintenance is desired, e.g. from about 2 to about 5 times per week.

We have unexpectedly found that the above-described cleansing composition and cleansing system are capable of efficiently mediating the deposition and permeation of various benefit agents, such as antidandruff agents, onto and into the skin following topical administration thereto. More specifically, we have surprisingly found that when benefit agents are combined with either the cleansing composition or the cleaning system of the present invention, the amount of benefit agents deposited onto and/or into the skin, hair, and/or nails is about 50% greater than the amount of benefit agents deposited onto and/or into the skin, hair, and/or nails after application of known, commercial benefit agent-containing cleansers.

An alternative preferred embodiment of the present invention is directed to a method for treating hair loss, such as hair loss resulting from alopecia, comprising topically applying the above-described cleaning system and the hair loss benefit agent to a desired location on an animal or human, wherein the benefit agent is comprised of an effective amount of a hair loss treatment agent such as minoxidil or mixture thereof. As used herein, "hair loss treatment agents" shall include agents capable of growing hair and/or agents capable of preventing the loss of hair. By "effective amount," it is meant an amount effective for treating hair loss and preferably may range from, based upon the total weight of the cleansing system, from about 0.001 percent to about 20 percent, and preferably from about 1 percent to about 5 percent.

Examples of benefit agents suitable for treating hair loss include, but are not limited to potassium channel openers or peripheral vasodilators such as minoxidil, diazoxide, and compounds such as N*-cyano-N-(tert-pentyl)-N'-3pyridinyl-guanidine ("P-1075") as disclosed in U.S. Pat. No. : 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin El and prostaglandin F2-alpha; fatty acids, such as oleic acid; dirurectics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Jobo-randi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof.

Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

Another embodiment of the present invention is directed to a method for inhibiting hair growth comprising topically applying the above-described composition/system combined with a benefit agent to a desired area on an animal or human for inhibiting hair growth, wherein the benefit agent is comprised of an effective amount of a hair growth inhibiting agent. In a preferred embodiment, the cleaning system contains, based upon the total weight of the cleaning system, from about 0.001 percent to about 20 percent, and preferably from about 0.01 percent to about 5 percent hair growth inhibiting agent.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Preferred hair growth inhibitory agents include serene proteases, retinol, isotretinoin, betamethoisone, alpha-tocophenol and derivatives thereof, or mixtures thereof.

Another preferred embodiment of the present invention is directed to a method for treating acne and for reducing the signs of aging, i.e. wrinkles, fine lines, and other manifestations of photodamage, comprising topically applying the above-described cleaning system and the relevant benefit agent to the skin of an animal or human at a desired area, wherein the benefit agent is comprised of an effective amount of an anti-acne agent or an anti-aging agent, respectively.

Examples of suitable anti-aging agents include, but are not limited to inorganic sunscreens such as titanium dioxide and zinc oxide; organic sunscreens such as octyl-methoxy cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaprolc acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, antioxidants, alpha-hydroxy acids and beta-hydroxy acid with retinol and tretinoin being most preferred.

Suitable amounts of anti-aging agents include, based upon the total weight of the described cleaning system, from about 0.01 percent to about 20 percent, and preferably from about 0.04 percent to about 5 percent.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as alnus, arnica, artemisia capillaris, asiasarum root, birrh, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata; imidazoles such as ketoconazole and elubiol, and those described in Gollnick, H et al. 196(I) Dermatology Sebaceous Glands, Acne and Related Disorders, 119–157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Suitable amount of anti-acne agents include, based upon the total weight of the described cleaning system, from about 0.01 percent to about 10 percent, and preferably from about 0.04 percent to about 5 percent.

Another preferred embodiment of the present invention is directed to a method for depigmenting the skin, comprising topically applying to skin at a desired area the above-described cleaning system and an effective amount of the depigmentation benefit agent. Suitable effective amounts of depigmentation agents include, based upon the total weight of the described cleaning system, from about 0.01 percent to about 10 percent, and preferably from about 0.04 percent to about 5 percent.

Examples of suitable depigmentation agents include, but are not limited to soy and derivatives thereof, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinol, Kojic acid, and hydroquinone, being preferred.

An alternative preferred embodiment of the present invention is directed to a method for treating the symptoms and/or the diseases of dandruff, seborrheic dermatitis and/or psoriasis, comprising topically applying the above-described cleaning system and the relevant benefit agent to a location desired wherein the benefit agent is comprised of an effective amount of a dandruff treatment agent, a seborrheic dermatitis treatment agent, or a psoriasis treatment agent, respectively. As used herein, "dandruff treatment agent," "seborrheic dermatitis treatment agent," or a "psoriasis treatment agent," respectively, shall include agents capable of treating the symptoms and/or the diseases of dandruff, seborrheic dermatitis, and psoriasis, respectively. By "effective amount," it is meant an amount effective for treating the disease and/or the symptoms associated therewith and preferably may range from, based upon the total weight of the cleaning system, from about 0.001 percent to about 10 percent, and preferably from about 0.01 percent to about 5 percent.

Examples of benefit agents suitable for treating the symptoms and/or the diseases of dandruff, seborrheic dermatitis and/or psoriasis, respectively, nonexclusively include those set forth above with shale oil and derivatives thereof, elubiol, ketoconazole, coal tar, salicylic acid, zinc pyrithione, selenium sulfide, hydrocortisone, sulfur, menthol, pramoxine hydrochloride, and mixtures thereof being particularly preferred.

The compositions of the present invention may be directed applied to the skin or may be applied onto other delivery implements such as wipes, sponges, brushes, and the like. The compositions may be used in products designed to be left on the skin, wiped from the skin, or rinsed off of the skin.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Oil in Water Emulsion Incorporating a Polymeric Emulsifier

Preparation of Lipophilic Phase:

11 g of PEG-30 dipolyhydroxystearate, available from Uniqema, Inc. under the tradename "Arlacel P-135," 50 g of isononyl isononanoate, available from Alzo, Inc. under the tradename, "Wickenol 151," 50 g of a mixture of hexyldecyl benzoate and butyloctyl benzoate, available from C.P. Hall Company under the tradename, "Hallstar AB," and 50 g of cyclomethicone available from Dow Corning under the tradename, "Dow 344 Fluid" were combined into a glass beaker containing a propeller stirrer and heated to a temperature of 60° C. until homogeneous.

Preparation of Hydrophilic Phase:

Into a primary glass beaker containing 795 g of deionized water, 5 g of PEG-8 caprylic/capric glycerides available from Trivent Inc. under the tradename, "Trivasol BW" was added thereto with stirring at 25° C. until homogeneous. For aiding in dispersion of the thickener in the formulation, 4 g of carbomer available from B.F. Goodrich, Inc. under the tradename, "Carbopol Ultrez" were added to 30 g of dimethylisosorbide available from Uniqema, Inc. under the tradename, "Arlasolve DMI" in a separate beaker with hand stirring. Into the dimethylisosorbide mixture was then added 2 g of methylparaben and 1 g of propylparaben with hand stirring until homogeneous to produce a pre-mixture. The pre-mixture was then added to the primary glass beaker with constant stirring until the resulting mixture was homogeneous.

Preparation of Final Composition:

The lipophilic phase was then added to the hydrophilic phase with constant stirring at 25° C. until homogeneous. 2 g of triethanolamine available from Union Carbide under the tradename, "Trolamine 99%" was then added to the resulting mixture with stirring until homogeneous.

Example 2

Preparation of Polymeric Emulsifier-Free Oil in Water Emulsion

Preparation of Lipophilic Phase:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," and 20 g of cyclomethicone available from Dow Corning under the tradename, "Dow 345 Fluid" were combined into a glass beaker at a temperature of 25° C. and stirred until homogeneous.

Preparation of Hydrophilic Phase:

Into a primary glass beaker containing 859.7 g of deionized water, 5 g of carbomer available from B.F. Goodrich, Inc. under the tradename, "Carbopol Ultrez" was added thereto with stirring at a temperature of 25° C. until homogenous. Into a separate beaker was added 7.5 g. of sucrose cocoate available from Croda, Inc. under the tradename, "Crodesta SL-40," 7.5 g. of PEG-6 Capric/caprylic glycerides available from Croda, Inc. under the tradename, "Glycerox 767," 10 g of hexylene glycol, 3 g. of methylparaben and 0.5 g of propylparaben with hand stirring until homogeneous to produce a pre-mixture. The pre-mixture was then added to the primary glass beaker with constant stirring until the resulting mixture was homogeneous.

Preparation of Final Composition:

After the lipophilic phase was added to the hydrophilic phase with constant stirring at 25° C. until homogeneous, 6.8 g. of a 20% aqueous solution of sodium hydroxide was then added thereto with stirring at a temperature of 25° C. The resulting mixture was then mixed for 15 minutes.

Example 3

Use of Emulsions to Remove Make-Up

Onto 3 respective ½ inch by 1 inch rectangle areas located on the forearms of Caucasian women were applied each of the make-ups described in Table A below:

TABLE A

Types of Make-Up

| Type of Make-up | Supplier | Tradename/Color |
|---|---|---|
| Foundation | Revlon | "Colorstay Make-Up"-in "Mocha" |
| Lipstick | Estee Lauder | "All Day Lipstick"-in "Regal Red" |
| Mascara | Revlon | "Colorstay Lashcolor Waterproof"-in "Navy" |

After dipping a wooden applicator from Scientific Products into the foundation, the foundation was spread throughout the designated area and evenly distributed therein with a finger cot.

The lipstick was directly applied to the designated area and evenly distributed therein with a finger cot.

The mascara was spread with its wand in the designated rectangular area and evenly distributed therein with a finger cot.

After the make-up dried for 30 minutes at room temperature, 0.8 ml of the emulsion of Example 1 was dispensed via syringe across all three test sites. Using a wooden tongue depressor, the emulsion was rubbed across all three test sites in a rapid, circular motion for 30 seconds. Then, each of the three test sites were gently wiped with a Kim-wipe.

This procedure was repeated but wherein the emulsion was replaced with the following respective cleansing products: a) "Galenic," which is available from Laboratoires Galenic, a division of PIERRE FABRE, under the tradename, "Lait Demaquillant Hydratant (Moisturizing Cleansing Milk);" b) "Cetaphil," which is available from GALDERMA INTERNATIONAL under the tradename, "Lotion Nettoyante/Haute Tolerance (pour peaux sensibles);" c) "pH 5.5 3-in-1," which is available from JOHNSON & JOHNSON LIMITED under the tradename, "JOHNSON's pH 5.5-3 in 1 Facial Cleanser;" d) "Vichy," which is available from VICHY LABORATORIES under the tradename, "Demaquillant Integral (a l'eau thermale apaisante);" e) "Oil of Olay," which is commercially available from THE PROCTER & GAMBLE COMPANY under the tradename, "Oil of Olay Facial Cleansing Lotion;" and f) "F # 8626-015," which is similar to the formulation as set forth in Example 2, except as follows in Table B below:

TABLE B

Contrast of Example 2 formulation with formula 8626-015:

| Example 2 Formulation | Modified Example 2 (F #8626-015) | Component |
|---|---|---|
| 0.3% (3 grams) | 0.2% (2 grams) | methylparaben |
| 0.05% (0.5 grams) | 0.1% (1 gram) | Propylparaben |
| 85.97% (859.7 grams) | 86.02% (860.2 grams) | Water |

Photographs of the test sites were obtained after the make-up was applied and after the three sites were rubbed with the above six products as shown in FIG. 1.

As evidenced in FIG. 1, the emulsion of modified Example 2 was superior with respect to removal of mascara, foundation, and lipstick in comparison to the other cleansers. The emulsion of Example 1 (not shown in FIG. 1) also was effective in removing all three types of make-up. This Example showed that the emulsions of the present invention are superior with respect to known commercial cleansers in removing a variety of makeup types from the skin.

Example 4

Preparation of Shower Gel Containing Sunscreen

A composition containing the following ingredients as set forth in Table C is prepared as follows;

TABLE C

Composition of Shower Gel Containing Sunscreen

| Tradename | Chemical Name | Weight (g) | Supplier |
|---|---|---|---|
| WATER PHASE | | | |
| — | Deionized water | 696.5 | — |
| — | Methylparaben | 3 | — |
| Comperian 100K | Cocamide MEA | 30 | Henkel Corporation |
| Planteren 1200N | Lauryl glucoside | 50 | Henkel Corporation |
| Schercomid HT 60 | PEG-50-Tallow Amide | 50 | Scher Chemical Corporation |
| | Hexylene glycol | 10 | |
| Standamox CAW | Cocamidopropylamine oxide | 50 | Henkel Corporation |
| OIL PHASE | | | |
| Hallstar AB | Hexyldecyl benzoate & butyloctyl benzoate | 50 | C.P. Hall Company |
| Arlacel P-135 | PEG-30 Dipolyhydroxy-stearate | 30 | Uniqema, Inc. |
| Neo Heliopan | Menthyl anthranilate | 30 | Haarmann & Reimer |
| POST ADDITION | | | |
| Crothix Liquid | PEG 150 pentaerythrityl tetrastearate & PEG-6 caprylic/capric glycerides & water | 10 | Croda Inc. |
| Kathon CG | Methylchloro-isothiazolinone & methylisothiazonlinone | 0.5 | Rohm & Haas |

After heating the deionized water to a temperature of about 75° C. to about 80° C. in a beaker, the hexylene glycol followed by the methylparaben is added thereto with mixing until solubilized. The cocamide MEA followed by the lauryl glucoside is then added thereto sequentially at constant temperature. The PEG-50 tallow amide is then melted and added to the resulting mixture at constant temperature. The cocamidopropylamine oxide is then added thereto at constant temperature to form a water phase premixture.

In another beaker, all of the oil phase components are combined with mixing at a temperature of about 75° C. to about 80° C. until uniform to form an oil phase premixture. The oil phase premixture is then added to the water phase premixture at constant temperature.

The "Crothix Liquid" component is then added thereto with mixing until uniform, then the temperature is lowered to about 50° C. The "Kathon CG" component is then added thereto, and the resulting mixture is cooled to room temperature.

The resulting cleansing formulation will possess excellent foaming properties and, after rinsing, will leave the skin with a light, moisturized feeling. Moreover, an effective amount of sunscreen agent will be deposited on the skin after rinsing the formulation from the skin with water.

Examples 5 and 6

Preparation of Foaming Anti-Acne Shower Gels

The composition of Example 5 containing the following ingredients as set forth in Table D is prepared as follows:

TABLE D

Compositions of Foaming Shower Gel

| Tradename | Chemical Name | Wt % Ex. 5 | Wt % Ex. 6 | Supplier |
|---|---|---|---|---|
| WATER PHASE | | | | |
| — | Deionized water | 49.440 | 49.654 | — |
| — | Methylparaben | 0.3 | 0.3 | — |
| Comperian 100K | Cocamide MEA | 3.0 | 3.0 | Henkel Corporation |
| Planteren 1200N | Lauryl glucoside | 5.0 | 5.0 | Henkel Corporation |
| Schercomid HT 50 | PEG-50 Tallow Amide | 5.0 | 5.0 | Scher Chemical Co. |
| Standamox CAW | Cocamidopropylamine oxide | 5.0 | 5.0 | Henkel Corporation |
| Schercoquat DAS | Quatemium 61 | 2.0 | 2.0 | Scher Chemical Co. |
| Jaguar C17 | Guar hydroxypropyl trimonium chloride | 0.5 | 0.5 | Rhodia |
| | Glycerin | 5.0 | 5.0 | — |
| | Deionized water | 10 | 10 | — |
| | Citric acid (20% soln) | 0.566 | 0.490 | — |
| OIL PHASE | | | | |
| Abil EM 90 | Cetyl dimethicone copolyol | 0.0 | 3.0 | Goldschmidt Chemical Corporation |
| Arlacel P-135 | PEG-30 Dipolyhydroxystearate | 3.0 | 0.0 | Unichema, Inc. |
| Wickenol 151 | Isononyl isononanoate | 1.0 | 1.0 | Alzo |
| Volpo L3 Special | Laureth-3 | 5.0 | 5.0 | Croda, Inc. |
| POST ADDITION | | | | |
| Arlasolve DMI | Dimethyl isosorbide | 4.0 | 4.0 | Croda Inc. |
| Salicylic acid | Salicylic acid | 2.0 | 2.0 | — |
| NaOH (10%) | Sodium hydroxide | 0.144 | none | — |
| Kathon CG | Methyl-chloroisothiazolinone & methylisothiazolinone | 0.050 | 0.050 | Rohm & Haas |

Preparation of Hydrophilic Phase

The water phase premixture is prepared in accordance with Example 3, but with the following additional steps: The quaternium-61 is added with mixing to the mixture after the addition of the cocamidopropyl amine oxide thereto at constant temperature until homogeneous.

In a separate glass beaker equipped with a propeller, the guar hydroxypropyl trimonium chloride and the glycerin are combined with stirring. The additional deionized water is then slowly added thereto with constant stirring. The resulting mixture is then mixed for about 15 minutes, then acidified with the citric acid solution. The acidified solution is then added to the water phase premixture with stirring at a temperature of about 75° C. to about 80° C. until homogeneous.

Preparation of Oil Phase

PEG-30 dipolyhydroxystearate is combined with the laureth-3 in another beaker with mixing at a temperature of about 75° C. to about 80° C. to form an oil phase premixture.

The oil phase premixture is then added to the water phase premixture with mixing at constant temperature.

Preparation of Final Composition:

The lipophilic phase is added to the hydrophilic phase with constant stirring at 75° C. until homogenous. After the temperature of the resulting mixture is lowered to 50° C. with continuous stirring, a premixed solution of 40 grams of Dimethyl Isosorbide available from Uniqema Inc. under the tradename "Arlasolve DMI" and 20 grams of salicylic acid are added thereto with stirring. After the temperature of the resulting mixture is lowered to 30° C., its pH is adjusted to approximately 3.1 by adding 1.4 grams of a 10% aqueous sodium hydroxide solution with continued stirring until the temperature of the resulting mixture reaches 25° C.

This process is repeated for the formulation of Example 6, but the PEG-30 dipolyhydroxystearate is replaced with cetyl dimethicone copolyol.

The above formulations will result in gels that possess good foaming properties as well as leave the skin with a pleasant, lightly moisturized "after feel" due to the effective deposition of the humectant. Similarly, the formulations will be useful as anti-acne formulations due to their ability to effectively deposit the salicylic acid component into and onto the skin.

Example 7

Preparation of Foaming Gel Containing Sunscreen

Preparation of Hydrophilic Phase:

Into a primary glass beaker equipped with a propeller containing 667 grams of deionized water, 30 grams of Hexylene Glycol available from Shell Chemical Company and 3 grams of methylparaben are added thereto stirring at 75° C. until homogenous. While maintaining the agitation and temperature as constant, 30 grams of cocomonoethanolamide (100% active) available from Henkel Corporation under the tradename "Comperlan 100K", 50 grams of Lauryl Glucoside (50% active) available from Henkel Corporation under the tradename "Plantaren 1200N", 50 grams of PEG-50 Tallow Amide (100% active) available from Scher Chemical Corporation under the tradename "Schercomid HT 60", and 50 grams of Cocamidopropylamine Oxide (30% active) available from Henkel Corporation under the tradename "Standamox CAW" are added to this aqueous mixture and mixed until homogenous.

Preparation of Lipophilic Phase:

50 grams of Hexyldecyl Benzoate and Butyloctyl Benzoate available from C.P. Hall Co. under the tradename "HallStar AB", 30 grams of PEG-30 Dipolyhydroxystearate available from Unichema, Inc. under the tradename "Arlacel P135" and 30 grams of Menthyl Anthranilate available from Haarmann & Reimer Corp. under the tradename "Neo Heliopan MA" are combined into another glass beaker equipped with a propeller and stirred until homogenous with heat until the resulting lipophilic mixture was at a temperature of 75° C.

Preparation of Final Composition:

The lipophilic phase is then added to the hydrophilic phase with constant stirring at 75° C. 10 grams of a mixture of PEG-150 Pentaerythrityl Tetrastearate, PEG-6 Caprylic/Capric Glycerides, and Water available from Croda Inc. under the tradename "Crothix Liquid" is then added thereto. The resulting mixture is then stirred at 75° C. unto homogenous, then cooled to room temperature with constant stirring.

The resulting cleansing formulation possesses excellent foaming properties and, after rinsing, leaves the skin with a light, moisturized feeling. The formulation also effectively deposits the sunscreen agent into and onto the skin.

Example 8

Pr paration of Foaming Acne Wash
Preparation of Hydrophilic Phase:

Into a primary glass beaker equipped with a propeller stirrer containing 414.9 grams of deionized water, 3 grams of methylparaben are added thereto at 75° C. until homogenous. While maintaining constant agitation and temperature, 30 grams of cocomonoethanolamide (100% active) available from Henkel Corporation under the tradename "Comperlan 100K", 50 grams of Lauryl Glucoside (50% active) available from Henkel Corporation under the tradename "Plantaren 1200N", 50 grams of PEG-50 Tallow Amide (100% active) available from Scher Chemical Corporation under the tradename "Schercomid HT 60", 50 grams of Cocamidopropylamine Oxide (30% active) available from Henkel Corporation under the tradename Standamox CAW, and 20 grams of Quaternium-61 (90% active) available from Scher Chemical Corporation under the tradename "Schercoquat DAS" are added to this aqueous mixture and mixed until homogenous to form a primary hydrophilic phase.

5 grams of Guar Hydroxypropyl Trimonium Chloride available from Rhodia Inc. under the tradename "Jaguar C17" is combined with stirring with 50 grams of glycerin into a separate glass beaker equipped with a propeller stirrer. 100 grams of deionized water is slowly added with mixing to this mixture at constant temperature. After the resulting mixture is mixed for 15 minutes until homogenous, the mixture is acidified with 5.7 grams of a 20% aqueous solution of citric acid. After the acidified mixture is added to the primary hydrophilic phase, the resulting hydrophilic mixture is stirred at 75° C. until homogenous.
Preparation of Lipophilic Phase:

50 grams of isopropyl PPG-2-Isodeceth-7 Carboxylate available from Clariant Corporation under the tradename "Velsan D8P-3", 30 grams of PEG-30 Dipolyhydroxystearate available from Unichema, Inc. under the tradename "Arlacel P135" and 30 grams of Laureth-3 (100% active) available from Croda Inc. are combined with stirring into a glass beaker equipped with a propeller stirrer until homogenous and heated to a temperature of 75° C.
Preparation of Final Composition:

The lipophilic phase is added to the hydrophilic phase with constant stirring at 75° C. until homogenous. After the temperature of the resulting mixture is lowered to 50° C. with continuous stirring, a premixed solution of 40 grams of Dimethyl Isosorbide available from Unichema Inc. under the tradename "Arlasolve DMI" and 20 grams of salicylic acid is added thereto with stirring. After the temperature of the resulting mixture is lowered to 30° C., its pH is adjusted to approximately 3.1 by adding 1.4 grams of a 10% aqueous sodium hydroxide solution with continued stirring until the temperature of the resulting mixture reaches 25° C.

The resulting wash product will not only possess excellent foaming properties but will also be an effective anti-acne product due to its ability to deposit the anti-active agent into and onto the skin.

Example 9

Preparation of Water-in-Oil Emulsion
Preparation of Lipophilic Phase:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," and 20 g of cyclomethicone available from Dow Corning under the tradename, "Dow 345 Fluid" were combined into a glass beaker at a temperature of 25 ° C. and stirred until homogeneous.
Preparation of Hydrophilic Phase:

Into a primary glass beaker containing 859.7 g of deionized water, 5 g of carbomer available from B.F. Goodrich, Inc. under the tradename, "Carbopol Ultrez" was added thereto with stirring at a temperature of 25° C. until homogenous. Into a separate beaker was added 7.5 g. of sucrose cocoate available from Croda, Inc. under the tradename, "Crodesta SL-40," 7.5 g. of PEG-6 Capric/caprylic glycerides available from Croda, Inc. under the tradename, "Glycerox 767,"10 g of hexylene glycol, 3 g. of methylparaben and 0.5 g of propylparaben with hand stirring until homogeneous to produce a premixture. The pre-mixture was then added to the primary glass beaker with constant stirring until the resulting mixture was homogeneous.
Preparation of Final Composition:

After the 6.8 g. of a 20% aqueous solution of sodium hydroxide was added to the hydrophilic phase with constant stirring at 25° C. until homogeneous, the lipophilic phase was added thereto with stirring at a temperature of 25° C. The resulting mixture was then mixed for 15 minutes.

Example 10

Preparation of Oil-in-Water Emulsion Containing Retinol

Preparation of Lipophilic Phase:

11 g of PEG-30 dipolyhydroxystearate, available from Uniqema, Inc. under the tradename "Arlacel P-135," 50 g of isononyl isononanoate, available from Alzo, Inc. under the tradename, "Wickenol 151," and 50 g of a mixture of hexyldecyl benzoate and butyloctyl benzoate, available from C.P. Hall Company under the tradename, "Hallstar AB" were combined with continous mixing in a vessel and heated to a temperature of 45° C. until homogeneous. After the mixture was cooled to a temperature of 25° C., 50 g of cyclomethicone available from Dow Corning under the tradename, "Dow 344 Fluid" and 6.9 g of a mixture of vitamin A alcohol and polysorbate 20 in a 1:1 weight ratio were added thereto with continuous mixing under an Argon blanket and under yellow light into a glass beaker containing a propeller stirrer until homogeneous. All subsequent procedures with this lipophilic phase were conducted under these conditions of argon blanket and yellow light until the formulation is placed into an oxygen and light impermeable container.
Preparation of Hydrophilic Phase:

Into a primary glass beaker containing 795 g of deionized water, nitrogen was bubbled therein until the subsequent addition of the lipophilic phase thereto so as to minimize exposure to oxygen. 5 g of PEG-8 caprylic/capric glycerides available from Trivent Inc. under the tradename, "Trivasol BW" was then added thereto with stirring at 25° C. until homogeneous. For aiding in dispersion of the thickener in the formulation, 4 g of carbomer available from B.F. Goodrich, Inc. under the tradename, "Carbopol Ultrez" were added to 30 g of dimethylisosorbide available from Uniqema, Inc. under the tradename, "Arlasolve DMI" in a separate beaker with hand stirring. Into the dimethylisosorbide mixture was then added 2 g. of methylparaben and 1 g of propylparaben with hand stirring until homogeneous to produce a pre-mixture. The pre-mixture was then added to the primary glass beaker with constant stirring until the resulting mixture was homogeneous.

Preparation of Final Composition:

The lipophilic phase was then added to the hydrophilic phase with constant stirring at 25° C. until homogeneous. 2 g of triethanolamine available from Union Carbide under the tradename, "Trolamine 99%" was then added to the resulting mixture with stirring until homogeneous. The final emulsion contains the components as set forth in Table E:

TABLE E

Emulsion Components

| Chemical Name | Trade Name | % (wt/wt) |
|---|---|---|
| PEG-30 dipolyhydroxystearate | Arlacel P-135 | 1.1 |
| Isononyl isononanoate | Wickenol | 5.0 |
| Hexyldecyl benzoate and butyloctyl benzoate | Hallstar AB | 5.0 |
| Cyclomethicone | Dow 344 Fluid | 5.0 |
| Vitamin A alcohol and Tween 20 | Retinol 50C | 0.69 |
| Water | Water | 78.81 |
| Carbomer | Carbopol Ultrez | 0.40 |
| PEG-8 caprylic/capric glycerides | Trivasol BW | 0.50 |
| Methylparaben | Methylparaben | 0.20 |
| Propylparaben | Propylparaben | 0.10 |
| Dimethyl isosorbide | Arlasolve DMI | 3.0 |
| triethanolamine | Trolamine 99% | 0.2 |

Example 11

Preparation of Water-in-Oil Emulsion Containing Retinol

Preparation of Lipophilic Phase:

11 g of PEG-30 dipolyhydroxystearate, available from Uniqema, Inc. under the tradename "Arlacel P-135," 30 g of isononyl isononanoate, available from Alzo, Inc. under the tradename, "Wickenol 151," and 30 g of a mixture of hexyldecyl benzoate and butyloctyl benzoate, available from C.P. Hall Company under the tradename, "Hallstar AB" were combined in a vessel with mixing and heated to a temperature of 45° C. until homogeneous. After the resulting mixture was cooled to a temperature of 25° C., 30 g of cyclomethicone available from Dow Corning under the tradename, "Dow 344 Fluid" and 6.9 g of a mixture of vitamin A alcohol and polysorbate 20 in a 1:1 weight ratio were added thereto with continuous mixing under an Argon blanket and under yellow light into a glass beaker containing a propeller stirrer until homogeneous. All subsequent procedures with this lipophilic phase was conducted under these conditions of argon blanket and yellow light until the formulation is placed into an oxygen and light impermeable container.

Preparation of Hydrophilic Phase:

Into a primary glass beaker containing 863.2 g of deionized water, nitrogen was bubbled therein in order to eliminate dissolved oxygen contained therein. The nitrogen continued to be bubbled therein until the subsequent addition of the lipophilic phase thereto. 5 g of PEG-8 caprylic/capric glycerides available from Trivent Inc. under the tradename, "Trivasol BW" was then added thereto with stirring at 25° C. until homogeneous. For aiding in dispersion of the thickener in the formulation, 4 g of carbomer available from B.F. Goodrich, Inc. under the tradename, "Carbopol Ultrez" were added to 10 g of triisopropyl citrate available from Phoenix Chemical Company under the tradename, "PELEMOL TIPC" in a separate beaker with hand stirring. Into the triisopropyl citrate mixture was then added 2 g. of methylparaben and 1 g of propylparaben with hand stirring until homogeneous to produce a pre-mixture. The pre-mixture was then added to the primary glass beaker with constant stirring until the resulting mixture was homogeneous.

Preparation of Final Composition:

2 g of triethanolamine available from Union Carbide under the tradename, "Trolamine 99%" was then added to the hydrophilic phase with constant stirring at 25° C. until homogeneous. The resulting mixture was then added to the lipophilic phase at constant temperature with stirring until homogeneous. The final emulsion contains the components as set forth in Table F:

TABLE F

Emulsion Components

| Chemical Name | Trade Name | % (wt/wt) |
|---|---|---|
| PEG-30 dipolyhydroxystearate | Arlacel P-135 | 1.1 |
| Isononyl isononanoate | Wickenol | 3.0 |
| Hexyldecyl benzoate and butyloctyl benzoate | Hallstar AB | 3.0 |
| Cyclomethicone | Dow 344 Fluid | 3.0 |
| Vitamin A alcohol and Tween 20 | Retinol 50C | 0.69 |
| Water | Water | 86.320 |
| Carbomer | Carbopol Ultrez | 0.40 |
| PEG-8 caprylic/capric glycerides | Trivasol BW | 1.0 |
| Methylparaben | Methylparaben | 0.20 |
| Propylparaben | Propylparaben | 0.10 |
| Triisopropyl citrate | Pelemol TIPC | 1.0 |
| NaOH | NaOH | 0.190 |

Example 12

Luminosity of the Formulation of Example 10

Figure 3A:
FIGS. 3 (a) and (b) are representations that illustrate the right side (FIG. 3(a)) and left side (FIG. 3(b)) of a subject's face prior to treatment as viewed under a CG-395 Filter.
FIGS. 3(c) and (d) are representations that illustrate the right side (FIG. 3(c)) and left side (FIG. 3(d)) of a subject's face while possessing the formulation of Example 10 as viewed under a CG-395 Filter.
FIG. 3(e) is a representation that illustrates the right side of a subject's face after the treatment of Example 10 was rinsed therefrom as viewed under a CG-395 Filter.
FIG. 3(f) is a representation that illustrates the left side of a subject's face after the treatment of Example 10 was wiped therefrom as viewed under a CG-395 Filter.
Figure 3B:
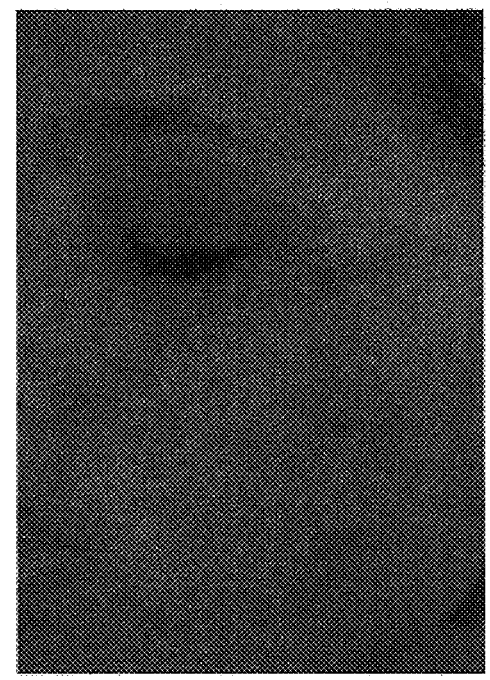

Digital images of the right side and the left side of a Caucasian woman's face was taken using a digital camera available from Fujix (Model No.: DCS 505) equipped with a 60 mm macro lens under strobe light conditions at F8 and 1/125 seconds. The camera lens was filtered with a CG-395 filter, and the strobe light source was filtered with a combination of a UG-11 filter and a KG-5 filter. These images are illustrated in FIG. 3(a) and FIG. 3(b), respectively.

Figure 3C:
Figure 3D:

After approximately 0.09 grams of the 0.3% retinol formulation prepared in Example 10 was applied to about a 20 $cm^2$ site on the suborbital (cheek) area of the right side and the left side of the woman's face, digital images were taken thereof under the above conditions as illustrated in FIG. 3(c) and FIG. 3(d), respectively. Using PHOTOSHOP software available from Adobe Inc., the digital image of each site was analyzed for average pixel intensity or luminosity. Luminosity, as used herein, is an indication of brightness of a given area as measured on a scale of 1 to 255, wherein the latter is the most luminescent. Using the 0.3% retinol concentration value, the pixel intensity change, as determined by the difference in pixel intensity between the base surface and the treated surface, for both the treated right side and left side of the face was plotted as a function thereof as illustrated in FIG. 5 (a).

Figure 3E:
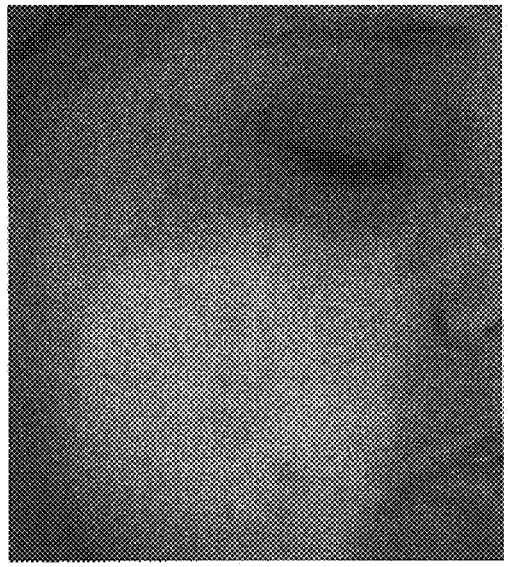
Figure 3F:
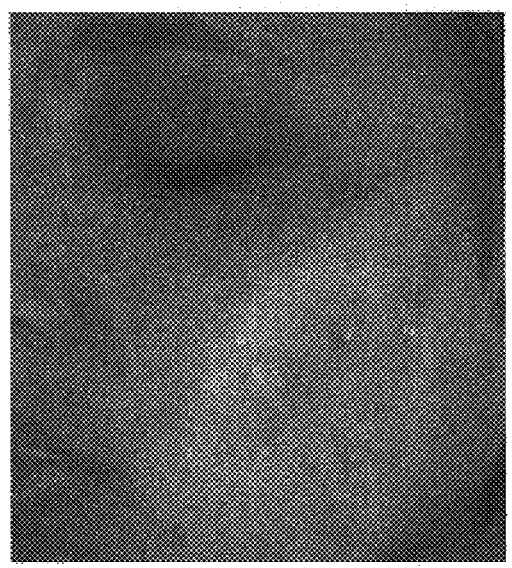

The formulation was then rinsed from the right side of the face, and a digital image was taken of the site under the above conditions as illustrated in FIG. 3(e). The formulation was then wiped twice using a Kimwipe tissue available from Kimberly Clark from the left side of the face, and a digital image was taken of the site under the above conditions as illustrated in FIG. 3(f). The pixel intensity change for the rinsed right side and the wiped left side was plotted on the graph of FIG. 5(a), then the respective deposited retinol concentrations were interpolated therefrom to be 0.145% and 0.1%, respectively.

This Example showed that the formulation of the present invention is not only a cleanser, but it also effectively deposits active agents, such as retinol, onto the skin. A significant amount of the agents remained on the skin after the formulation was removed therefrom. Moreover, this Example highlighted that when the cleanser composition of the present invention contains a 0.3% retinol active agent, it deposited the same amount of retinol on the skin as a leave-on product containing 0.145% retinol (when the compositions was removed via rinsing with water) and a leave-on product containing a 0.1% retinol (when the composition was removed via wiping).

Example 13

Luminosity of the Formulation of Example 11

Figure 4A:
FIGS. 4 (a) and (b) are representations that illustrate the right side (FIG. 4(a)) and left side (FIG. 4(b)) of a subject's face prior to treatment as viewed under a CG-395 Filter.
FIGS. 4(c) and (d) are representations that illustrate the right side (FIG. 4(c)) and left side (FIG. 4(d)) of a subject's face while possessing the formulation of Example 10 as viewed under a CG-395 Filter.
FIG. 4(e) is a representation that illustrates the right side of a subject's face after the treatment of Example 10 was rinsed therefrom as viewed under a CG-395 Filter.
FIG. 4(f) is a representation that illustrates the left side of a subject's face after the treatment of Example 10 was wiped therefrom as viewed under a CG-395 Filter.
Figure 4B:
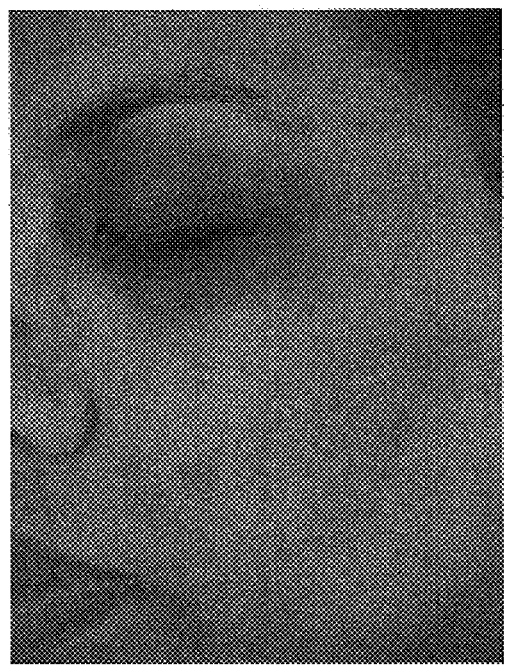

The procedure set forth in Example 12 was repeated using the formulation of Example 11 instead of that of Example 10. The pre-treatment images are illustrated in FIG. 4(a) and FIG. 4(b), respectively.

Figure 4C:
Figure 4D:
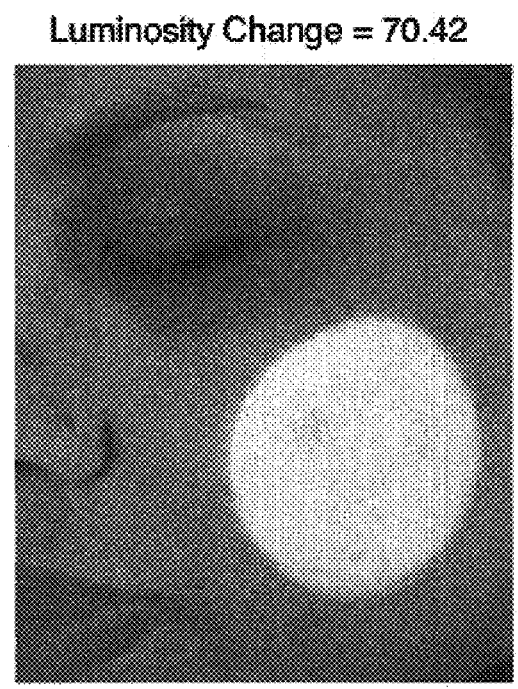

The formulation-containing images are illustrated in FIG. 4(c)(right side) and FIG. 4(d)(left side). Using the 0.3% retinol concentration value, the pixel intensity change for the treated right side and left side of the face was plotted as a function thereof as illustrated in FIG. 5 (d).

Figure 4E:
Figure 4F:
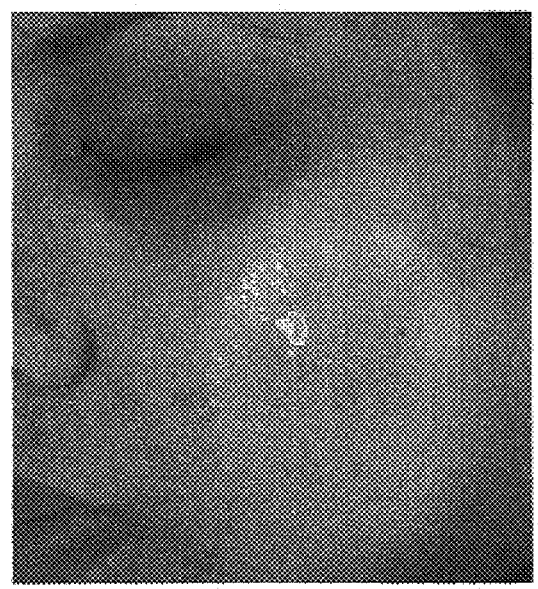

The digital image of the washed site is illustrated in FIG. 4(e), and the image of the wiped side is illustrated in FIG. 4(f). The pixel intensity change for the rinsed right side and the wiped left side was plotted on the graph of FIG. 5(b), then the respective deposited retinol concentrations were interpolated therefrom to be 0.135% and 0.072%, respectively.

This Example showed that the formulation of the present invention was not only a cleanser, but it also effectively deposited active agents, such as retinol, onto the skin. These agents remained present on the skin after the formulation was removed therefrom. Moreover, this Example highlighted that when the cleanser composition of the present invention contained a 0.3% retinol active agent, the cleanser deposited the same amount of retinol on the skin as a leave-on product containing 0.135% retinol (when the compositions was removed via rinsing with water) and a leave-on product containing a 0.072% retinol (when the composition was removed via wiping).

Example 14

Preparation of Oil-in-Water Emulsion Containing DMAE

Preparation of Lipophilic Phase:

10 g of steareth-2 available from Uniqema under the trade name "Brij 72", 8.5 g of isoceteth-20 also available from Uniqema under the tradename "Arlasolve 200", 10 g. of isononyl isononanoate available from Alzo, Inc., under the tradename "Wickenol 151", 10 g. of Isostearyl palmitate available from Brooks Industries under the tradename "Loronate OP", 10 g of cetyl octanoate, available from Brooks Industries, under the tradename "Loronate CIO," 10 g of pentaerythritol tetraoctanoate also available from Brooks Industries, under the tradename "Loronate PT," and 10 g of cyclomethicone available from Dow Corning under the tradename, "Dow 345 Fluid" were combined into a glass beaker at a temperature of 50° C. and stirred until homogeneous.

Preparation of Hydrophilic Phase:

602.5 g of deionized water were weighed into a primary glass beaker and heated to 78–82° C. With constant agitation, 4 g of PVM/MA Decadiene Cross polymer available from ISP under the tradename, "Stabileze QM" was added thereto and held at 78–82° C. until homogenous. This mixture was then cooled to 40–50° C., during which time, 1 g. of disodium EDTA, 10 g. of hexylene glycol, 7.5 g. of PEG-6 caprylic/capric glycerides available from Croda, Inc. under the tradename, "Glycerox 767", and 10 g. of PEG-150 pentaerythrityl tetrastearate also available from Croda under the tradename, "Crothix Liquid," were added to the primary beaker with constant stirring.

Preparation of Final Composition:

When both the lipophilic phase and the hydrophilic phase were at a temperature of 40° C.–50° C., the lipophilic phase was added to the hydrophilic phase with constant stirring. In a separate beaker, 30 g. of 2-(dimethylamino) ethanol, available from BASF under the tradename DMAE, and 50 g. of L-tyrosine available from Ajinimoto under the tradename "L-Tyrosine" were added to 150 g. of water, and mixed until homogenous. This premix was then added to the primary beaker with constant stirring. 10 g of Nylon-12 available from Kobo Products, Inc., under the tradename "SP-10", 5 g of talc available from Luzenac America under the tradename, "Windsor Talc 66", 10 g of silicone quaternium-13 available from Biosil Industries under the tradename, "Biosil Basics SPQ," and 10 grams of a phenoxyethanol, methylparaben, butylparaben, ethylparaben and propylparaben solution available from Nipa under the tradename "Phenonip" were added separately to the primary beaker with constant stirring. The entire mixture was adjusted to a pH of 7.0–7.5 with a 70% aqueous solution of glycolic acid, and homogenized for 2 minutes at medium power with a Gifford-Wood homogenizer.

After about 1 ml to about 10 ml of the resulting formulation is applied to the facial skin of consumers, the consumers perceive that their facial skin appears and feels firmer and "lifted."

Example 15

Preparation of Oil in Water Emulsion Containing a Polymeric Emulsifier and Colloidal Oat Flour Preparation of Hydrophilic Phase:

Into a primary glass beaker containing 850.70 g of deionized water, 10 g of Colloidal Oat Flour available from Quaker was added thereto with stirring at 25° C. until a homogeneous, smooth slurry was achieved. 2.5 g. of Acrylates/C10-30 Alkyl Acrylate Crosspolymer available from B.F. Goodrich, Inc. under the tradename, "Pemulen TR-1" and 2.5 g. of Carbomer, also available from B.F. Goodrich, Inc. under the tradename "Carbopol Ultrez" were then added to the primary beaker and mixed with slower agitation until homogenous. Into a separate beaker was added 7.5 g. of sucrose cocoate available from Croda, Inc. under the tradename, "Crodesta SL-40," 7.5 g. of PEG-6

Capric/caprylic glycerides available from Croda, Inc. under the tradename, "Glycerox 767," 10 g of hexylene glycol, 3 g. of methylparaben and 0.5 g of propylparaben with hand stirring until homogeneous to produce a pre-mixture. The pre-mixture was then added to the primary glass beaker with constant stirring until the resulting mixture was homogeneous.

Preparation of Final Composition:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," and 20 g of cyclomethicone available from Dow Corning under the tradename, "Dow 345 Fluid" were each added separately to the primary beaker with constant stirring at 25° C. until homogeneous. 2.5 g of Tetrasodium EDTA and, 6.8 g. of a 20% aqueous solution of sodium hydroxide was then added thereto with stirring at a temperature of 25° C. The resulting mixture was then mixed for 15 minutes.

Example 16

Preparation of Oil in Water Emulsion Containing a Polymeric Emulsifier and Colloidal Oat Flour Preparation of Preservative Pre-Blend 4 g of methylparaben, 1 g of propylparaben, 7.5 g of PEG-6 capric/caprylic glycerides available from Croda, Inc. under the tradename, "Glycerox 767," 7.5 g of sucrose cocoate also available from Croda, Inc. under the tradename, "Crodesta SL-40," and 10 g of hexylene glycol were combined with mixing under ambient conditions until homogeneous.

Preparation of Emulsion:

Into a primary glass beaker containing 852.5 g of Purified Water (USP), 10 g of Colloidal Oat Flour available from Quaker were added thereto with stirring at about 200 rpm and a temperature of about 20° C. to about 30° C. until a homogeneous, smooth slurry was achieved. 2.5 g. of Acrylates/C10-30 Alkyl Acrylate Crosspolymer available from B.F. Goodrich, Inc. under the tradename, "Pemulen TR-1" and 2.5 g. of Carbomer, also available from B.F. Goodrich, Inc. under the tradename "Carbopol Ultrez" were then added thereto and mixed with slower agitation until homogenous. After adding the Preservative Pre-blend with increased mixing at about 200 rpm thereto, the following components were sequentially added thereto with constant stirring at about 20° C. to about 30° C. until homogeneous, with intervals of 5 minutes between the addition of each respective component: 20 g of isononyl isononanoate, available from Alzo, Inc. under the tradename, "Wickenol 151," 20 g of cyclomethicone available from Dow Corning under the tradename, "Dow 345 Fluid", 20 g of isostearyl palmitate, available from Brooks Industries, under the tradename "Loronate OP," 20 g of cetyl octanoate, available from Brooks Industries, under the tradename "Loronate CIO," 20 g of pentaerythritol tetraoctanoate available from Brooks Industries, under the tradename "Loronate PT." 2.5 g of Tetrasodium EDTA and enough of a a 20% aqueous solution of sodium hydroxide was then added thereto with stirring at a temperature of about 20° C. to about 30° C. to produce a final mixture having a pH of 5.9 to 6.5. The resulting mixture was then mixed until homogeneous.

Example 17

Consumer Testing of Formulation of Example 16 Formula

One hundred and twenty-five mothers of babies aged 24 months and younger used both the formulation prepared in accordance with Example 16 as well as a cleanser available from Galderma Laboratories, Inc. under the tradename, "CetaPhil Gentle Skin Cleanser."

The mothers used each product for a minimum of at least 3 to 7 times for a one week period. When using the product in a rinse-off fashion, the mothers first poured the product onto a moistened hand or wet cloth then applied the product to the desired location on the babies' skin. After rubbing the product gently on the skin, the product was rinsed therefrom with water. When using the product in a wipe-off fashion, the mothers applied a liberal amount to the desired location on the babies' skin and rubbed gently. The excess product was then removed therefrom with a soft cloth or tissue.

The results of the study are shown in Table G below:

TABLE G

Comparative Study of Example 16 Formulation to Cetaphil

| Characteristic that either Completely describes or very well describes the product at issue | Formulation of Example 16 | C taphil |
|---|---|---|
| 1) Good for Sensitive Skin | 87* | 82 |
| 2) Nonirritating to Skin | 92 | 91 |
| 3) Won't Dry or Irritate the Most Sensitive Skin | 89 | 78 |
| 4) Cleanses Extra Gently | 87 | 86 |
| 5) Good for Everyday or Regular Use | 94 | 84 |
| 6) Cleans Without Drying Skin | 92 | 85 |
| 7) Relieves Baby's Dry Skin | 74 | 65 |
| 8) Can Be Use With or Without Water | 93 | 83 |
| 9) Effectiveness as a Cleanser | 82 | 76 |
| 10) Good for Use All Over the Body | 90 | 85 |
| 11) Makes Baby's Skin Feel Soft and Smooth | 89 | 74 |
| 12) Helps Baby's Skin Look and Feel Healthier | 70 | 66 |
| 13) Helps Baby's Skin Retain its Natural Moisture | 82 | 72 |
| 14) Relieves Baby's Itchy Skin | 51 | 46 |
| 15) Leaves Baby's Skin Feeling Clean | 86 | 75 |
| 16) Won't Sting or Irritate Eyes | 54 | 54 |

*These numbers indicate the percentage of the mothers that indicated that the identified product possessed the given characteristic.

This Example showed that the cleanser of Example 16 significantly outperformed the commercial product with respect to the majority of characteristics set forth in Table G.

Example 18

Preparation of Oil-in-Water Emulsion with Non-Ionic Emulsifier

Preparation of Lipophilic Phase:

20 g of isostearyl palmitate, available from Brooks Industries, under the tradename "Loronate OP," 20 g of isononyl isononanoate, available from Alzo, Inc. under the tradename, "Wickenol 151," 20 g of cetyl octanoate, available from Brooks Industries, under the tradename "Loronate CIO," 20 g of pentaerythritol tetraoctanoate available from Brooks Industries, under the tradename "Loronate PT," were combined into a glass beaker at a temperature of 25° C. and stirred until homogeneous.

Preparation of Hydrophilic Phase:

Into a primary glass beaker containing 859.7 g of deionized water, 2 g of carbomer available from B.F. Goodrich, Inc. under the tradename, "Carbopol ETD 2020", and 1 g of C10–C30 alkyl acrylate/crosspolymer commercially available from B.F. Goodrich under the tradename, "Pemulen TR1" were added thereto with stirring at a temperature of 25° C. until dispersed. While heating the mixture to 75° C., 1.2 g of tromethamine, 1 g of EDTA, 7.5 g. of PEG-6 Capric/caprylic glycerides available from Croda, Inc. under the tradename, "Glycerox 767," 10 g of hexylene glycol, 4 g. of methylparaben and 1 g of propylparaben were added with constant stirring until the resulting mixture was homogeneous. After the mixture reached a temperature of 75° C., 10 g. of a mixture of sorbitan stearate and sucrose cocoate available from Uniqema under the tradename, "Arlatone 2121," were added thereto with stirring for 30 minutes at constant temperature.

Preparation of Final Composition:

After the lipophilic phase was heated to a temperature of 75° C., It was then added to the hydrophilic phase with constant stirring at 75° C. until homogeneous. After the mixture was then cooled to 35° C., 20 g of cyclomethicone available from Dow Corning under the tradename, "Dow 345 Fluid" was added thereto. After the mixture was cooled to 25° C., 0.4 g. of tromethamine was then added thereto with stirring at constant temperature such that the resulting mixture had a pH of 5.5.

Example 19

Comparison of Make-Up Removability

A waterproof mascara available from Gemey under the tradename "Waterproof Gemey Noir," is copiously coated on a 16 cm² area on a forearm. This area is then wiped four times with a cotton ball soaked with 2 ml of the formula of Example 2. Visual assessment of the area is noted. This procedure is repeated on the same area and a second visual assessment is noted. This procedure is repeated on the same area and a third visual assessment is noted.

This procedure is repeated on an alternative areas of the forearm, but wherein the cleanser of Example 2 is replaced with the cleanser of Example 18 and the cleanser available from Johnson's under the tradename, "Johnson's pH 5.5 3-in-1 Cleansing Lotion," respectively.

Although all three cleansers effectively remove the mascara, this Example shows that the cleansers of Example 2 and Example 18 remove mascara more quickly than the commercial cleanser. In addition, all three cleansers are aesthetically acceptable according to consumer standards.

Example 20

Comparison of Make-Up Removability of Impregnated Wipes

The formulation of Example 18 is prepared, but wherein: 1) the carbomer and the C10–C30 alkyl acrylate/crosspolymer were replaced with 1 g of xanthan gum; 2) and 30 g of C14–22 alkyl alcohol and C12–C20 alkyl glucoside emulsifier available from Seppic under the tradename "Montanov L" was also added to the lipophilic phase; and 3) and 4 g of C13–C14 isoparaffin/isostearyl isostearate/Na polyacrylate/polyacrylamide/polysorbate 60 available from Seppic under the tradename, "Sepigel 502," was added to the finished mixture as the final product was cooled to 25 C.

The emulsion was pumped on to a stack of 25 folded, uncoated spunlaced wipes comprised of a blend of about 35% polyester and 65% rayon In an amount equivalent to 325% of the total noncoated wipe weight.

The resulting wipes were then compared with Johnson pH5.5 3-in-1 Cleansing wipes and Pond's Cleansing Towelettes available from Unilever using the test method set forth in Example 19 wherein the cotton ball was replaced by the respective wipe.

This Example showed that the wipes prepared in accordance with this Example are more effective in removing waterproof mascara than the two commercial products as determined after the first, second, and third assessment. More specifically, the wipes of this Example were significantly superior to the Pond's wipes with respect to mascara removal as determined after the third visual assessment.

Example 21

Preparation of Cleansing Composition 20 g of cyclomethicone available from the Dow Corning Corporation under the tradename, "DOW CORNING 345," 15 g of hexylene glycol, and 65 g of a mixture of hexyl decyl benzoate and butyl octyl benzoate available from the C.P. Hall Company under the tradename, "Hallstar AB" are sequentially added to a vessel with mixing at about 100 rpm under ambient conditions until the final mixture is homogeneous.

The resulting cleansing composition is effective in removing debris such as makeup from the skin.

We claim:

1. A foaming composition comprising:
   a. hexylene glycol;
   b. pentaerythritol teraoctanoate;
   c. water;
   d. a foaming surfactant, and
   e. a liquid silicone, wherein the foaming surfactant has a column height of greater than about 20 mm as determined by the Miles-Ross Test and is selected from the group consisting of non-ionic surfactants, cationic surfactants, amphoteric surfactants, anionic surfactant and mixtures thereof.

2. A foaming composition comprising:
   a. hexylene glycol;
   b. pentaerythritol tetraoctanoate;
   c. water;
   d. a foaming surfactant, and
   e. at least one of the following:
      i) a polymeric emulsifer selected from the group consisting of polyethylene glycol-30 dipolyhydroxystearate; dimethicone copolyol; substituted acrylates; and mixtures thereof and/or a thickener;
      ii) a benefit agent; or
      iii) a nonionic emulsifier.

3. The composition of claim 2 wherein the thickener is selected from the group consisting of carbomers, acrylate copolymers, hydroxyethylcellulose modified with cetyl ether groups, polyvinylmethyl ether/maleic anhydride (PVM/MA) decadiene crosspolymer, and mixtures thereof.

4. The composition of claim 2 wherein the thickener is selected from the group consisting of acrylates/aminoacrylates copolymer, acrylates/steareth-20 methacrylate copolymer; acrylates/ceteth-20 itaconate copolymer, acrylates/steareth-20 itaconate copolymer, carbomers, modified hydroxycellulose, polyvinylacetate/maleic anhydride (PVA/MA) decadiene crosspolymer, and mixtures thereof.

5. The composition of claim 2 further comprised of a cleansing enhancer that is a nonfoaming surfactant and/or a non-ionic emulsifier.

6. The composition of claim 5 wherein the nonfoaming surfactant is selected from the group consisting of sucrose cocoate, sucrose stearate and mixtures thereof.

7. The composition of claim 5 wherein the non-ionic emulsifier is selected from the group consisting of isoceteth 20, oleth-2, mixture of PEG-40 hydrogenated castor oil and trideceth-9, Poloxamer 184, laureth-4, sorbitan trioleate, polyoxyethylene-(2) oleyl ether, sorbitan stearate, cetearyl glucoside, glyceryl oleate, and mixtures thereof.

8. The composition of claim 2 wherein the benefit agent is selected from the group consisting of vasoconstrictors, collagen enhancers, anti-edema agents, depigmentation agents; reflectants; detangling/wet combing agents; film forming polymers; humectants; amino acid agents; antimicrobial agents; allergy inhibitors; anti-acne agents; anti-aging agents; anti-wrinkling agents, antiseptics; analgesics; antitussives; antpruritics; local anesthetics; anti-hair loss agents; hair growth promoting agents; hair growth inhibitor agents; antihistamines; antiinfectives; inflammation inhibitors; anti-emetics; anticholinergics; vasoconstrictors; vasodilators; wound healing promoters; peptides, polypeptides and proteins; deodorants and anti-perspirants; medicament agents; skin emollients and skin moisturizers; skin firming agents, hair conditioners; hair softeners; hair moisturizers; vitamins; tanning agents; skin lightening agents; antifungals; depilating agents; shaving preparations; external analgesics; perfumes; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavenoids; sensates; antioxidants; skin conditioners; hair lighteners; chelating agents; cell turnover enhancers; coloring agents; pigments; sunscreens and mixtures thereof.

9. The system of claim 2 wherein the benefit agent is selected from the group consisting of feverfew, centella asiatica, olive leaf, wheat protein, oat oil, lycopene, DMAE, soy and derivatives thereof, colloidal oatmeal, sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

* * * * *